United States Patent
Some

(10) Patent No.: US 7,027,142 B2
(45) Date of Patent: Apr. 11, 2006

(54) OPTICAL TECHNIQUE FOR DETECTING BURIED DEFECTS IN OPAQUE FILMS

(75) Inventor: Daniel Some, Ashdod (IL)

(73) Assignee: Applied Materials, Israel, Ltd., Rehovot (IL)

( * ) Notice: Subject to any disclaimer, the term of this patent is extended or adjusted under 35 U.S.C. 154(b) by 321 days.

(21) Appl. No.: 10/423,354

(22) Filed: Apr. 25, 2003

(65) Prior Publication Data

US 2003/0206292 A1    Nov. 6, 2003

Related U.S. Application Data

(60) Provisional application No. 60/378,729, filed on May 7, 2002, provisional application No. 60/378,400, filed on May 6, 2002.

(51) Int. Cl.
    *G01N 21/00* (2006.01)
(52) U.S. Cl. .................... 356/237.1; 356/237.2
(58) Field of Classification Search .. 356/237.1–237.5, 356/630
    See application file for complete search history.

(56) References Cited

U.S. PATENT DOCUMENTS

| 5,959,735 A * | 9/1999 | Maris et al. ................. 356/632 |
| 2002/0135784 A1* | 9/2002 | Morath et al. .............. 356/630 |
| 2003/0123051 A1* | 7/2003 | McGrew ...................... 356/72 |

* cited by examiner

*Primary Examiner*—Michael P. Stafira
(74) *Attorney, Agent, or Firm*—Tarek N. Fahmi

(57) ABSTRACT

A local area of a sample is focally heated to produce a transient physical deformation. The surface of the structure is optically monitored while the heated area cools to a baseline temperature by illuminating the heated region with one or more probe beams from time to time and detecting returning light. In some embodiments heat dissipation within the structure is correlated with change in optical reflectivity over time. In other embodiments, surface deformation of the structure is correlated with changes in light scattering from the surface. Following application of a pump pulse and no more than 3 probe pulses, a time varying returning light signal is compared with a corresponding returning light signal from a reference. An anomaly in the sample is indicated by a deviation between the two signals. First-degree exponential decay curves may be constructed from the signals, and their decay constants compared.

46 Claims, 12 Drawing Sheets

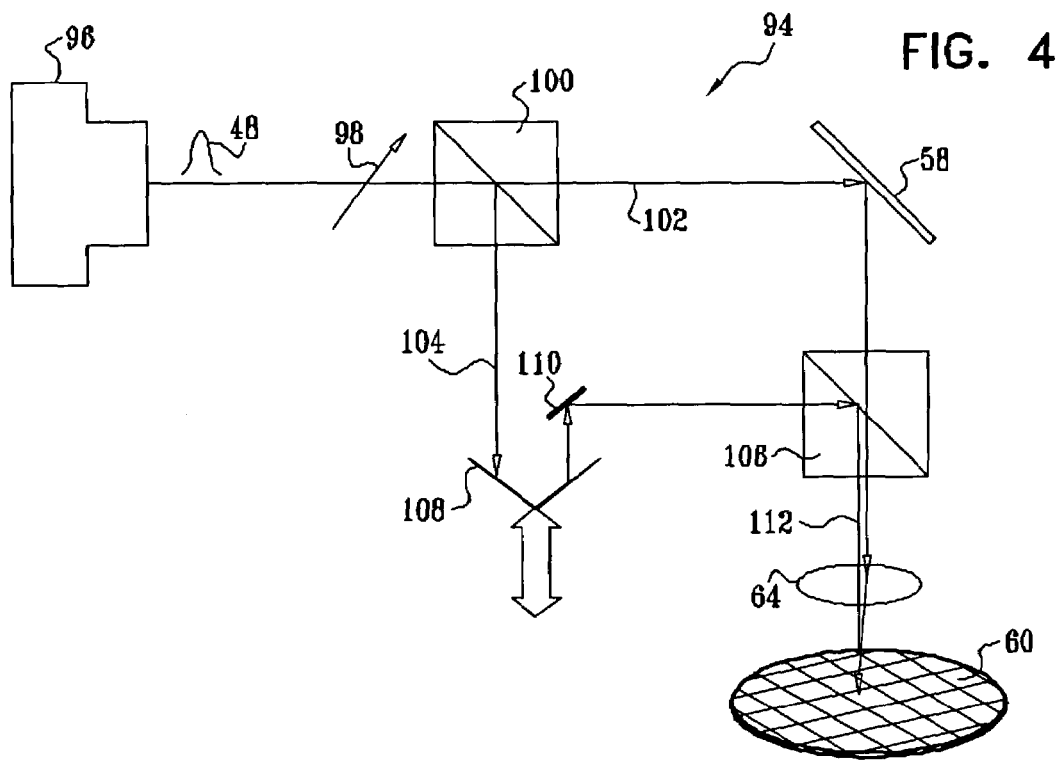
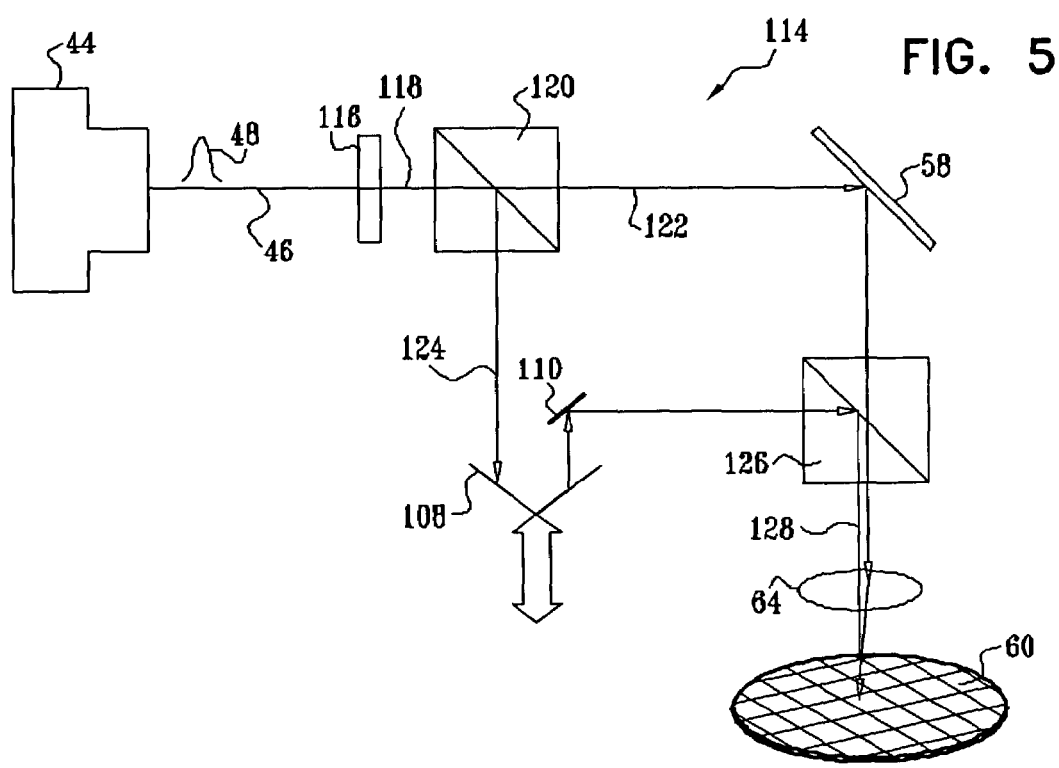

OPTICAL TECHNIQUE FOR DETECTING BURIED DEFECTS IN OPAQUE FILMS

CROSS-REFERENCE TO RELATED APPLICATIONS

This application claims the benefit of Provisional Application No. 60/378,729, titled Optical technique for detecting buried defects in opaque films" filed May 7, 2002 and claims the benefit of United States provisional patent application No. 60/378,400 filed 6$^{th}$ May 2002 titled "High speed laser inspection system".

BACKGROUND OF THE INVENTION

1. Field of the Invention

This invention relates to fabrication of semiconductor devices. More particularly, this invention relates to the detection of subsurface defects in non-homogeneous structures such as multilayered integrated circuits.

2. Description of the Related Art

Semiconductor structures are inspected prior to, during, and after patterning procedures. Patterned metal films used in integrated circuit devices are often created using a damascene technique, in which a pattern is etched in an insulating dielectric layer, and subsequently filled using any of several standard deposition techniques, e.g., chemical vapor deposition (CVD), physical vapor deposition (PVD), or electro-copper plating (ECP). In the course of this process defects may be created inside or under the metal, such as voids, delamination, underfill or underetch of the dielectric, and other interface-related defects.

Generally, these defects are not directly accessible using optical inspection techniques due to opacity of the surface layer. To some degree, they may be detected using voltage-contrast scanning electron microscopy (SEM), or electron beam inspection (EBI). Although buried defects can sometimes be seen using SEM, that technique is better adapted for evaluation of particular positions on a substrate or wafer, rather than for scanning. EBI is an inspection technique employing a scanning electron beam, which can scan significant portions of an entire wafer to automatically find defects. It can in principle see whatever a SEM tool sees. However, EBI tools are generally too slow and expensive for the production floor. They are typically used in the research and development stage of product development.

It is proposed in U.S. Pat. No. 4,710,030 to employ a pump beam of short, non-destructive laser pulses (0.01–100 ps duration) to induce a thermo-elastic deformation, or stress waves, in a structure being tested, and to monitor the transient response of the structure using a low-power laser probe beam that is directed to the area of the deformation. By analyzing the intensity of the returning probe beam, information regarding defects and other characteristics of the structure can be inferred.

Besides reflections of short-pulse-induced stress waves, voids and interface defects are known to produce other physical effects in response to a pump beam, such as changes in acoustic dispersion properties, and reduced heat dissipation. These effects are discussed in the document *Pico-second Ultrasonics*, Grahn et al., IEEE Journal of Quantum Electronics, Vol. 25 No. 12, pp. 2562–2568 (December 1989).

U.S. Pat. No. 5,633,711 discloses another example of monitoring the transient response to an excitation laser pulse that impinges on and locally heats a structure. In this disclosure, besides the intensity of the probe beam, phenomena such as acoustic oscillations and polarization disturbances are taken into account.

A disadvantage of the techniques disclosed in the above-noted patents is a low signal-to-noise ratio (SNR) in the detection signals. The stress wave produced by the pump beam is associated with very small changes in reflectivity (expressed as a percent of the light falling on the surface). Values from $1\times10^{-6}$ to $1\times10^{-4}$ are typical. It has thus been necessary to compensate for the poor SNR by repeating the detection sequence over a relatively long period, for example, a second for each detection spot. Many repetitions of the detection sequence are generally required to obtain meaningful data. Furthermore, the frequency of repetition is itself limited by the need to perform mechanical adjustments in the detection unit between performance cycles. Thus, the time needed to evaluate a structure becomes impracticably long for full-wafer inspection purposes.

U.S. Pat. No. 6,320,666 discloses an intensity modulated pump laser beam, which is focused onto a sample so as to excite the sample periodically. Periodic heating by the pump beam creates a time varying deformation in the sample surface. A probe laser beam, obtained from a second laser, is focused onto the sample within the periodically heated area. The pump and probe beam are spaced apart, and the probe beam is said to undergo periodic angular deviations at the frequency of the modulated heating. A photodetector is provided for monitoring the reflected power of the probe beam and generating an output signal responsively thereto. The output signal is filtered and processed to provide a measure of the modulated optical reflectivity of the sample. A steering apparatus is provided for adjusting the relative position of pump and probe beam spots on the sample surface. The steering apparatus is used to move the beam spots from an overlapping, aligned position, to a position of separation of up to about 10 microns. Measurements can be taken as the separation of the beam spots is gradually changed, or at discrete separation intervals. It is also proposed to increase information by varying the modulation frequency of the pump beam, and to obtain independent reflectivity measurements at a plurality of wavelengths using a polychromatic light source.

U.S. Pat. No. 5,748,317 discloses the use of laser time-delayed pump and probe beams for determining the thermal properties of thin film. Measurements of reflectance and other optical characteristics are used to estimate the Kapitza resistance of a film. Inferences regarding the structure of the film or interfaces therein are made using reference data obtained from simulation or from another sample. The technique requires quantitative conclusions to be drawn about a sample. This is relatively time-consuming and complex, and is not ideal for the rapid qualitative evaluation of production line output, which large wafers or similar specimens may need to be quickly evaluated.

It is proposed in U.S. Pat. No. 6,253,621 to analyze acoustic waves that are generated in a sample under test in response to a pulsed laser that is directed to a micro-spot on the sample and scanned. Acoustic waves are detected, and an acoustic index of refraction of a portion of the conductive structure is calculated as a function of the wave. The acoustic index of refraction is then spatially mapped over the sample. It is asserted that defects can be detected by intra-sample comparisons, or by comparison with a device that is known not to be defective.

The above-noted conventional techniques require extensive analysis of time-dependent signals. They are slow and computationally expensive.

SUMMARY OF THE INVENTION

The invention improves the quality and rapidity of detection of subsurface defects in non-homogeneous structures such as multilayered integrated circuits.

The invention detects buried defects in non-homogeneous structures such as multilayered integrated circuits without recourse to measurements requiring high sensitivity and extensive analysis of time-dependent signals.

The invention provides a method and system for transiently heating a local area of a structure to be tested and thereby producing a physical deformation therein. The surface of the structure is optically monitored while the area cools to a baseline temperature by illuminating the local area with one or more probe beams from time to time and detecting returning light from the probe beams. In some embodiments heat dissipation within the structure is correlated with changes in optical reflectivity over time. In other embodiments, surface deformation of the structure is correlated with changes in light that is scattered from the surface. A first-degree exponential decay curve is constructed from data obtained from light detectors of the scattered or reflected light, and its decay constant determined. A map may be produced by sequential application of the pump and probe beams to many regions of the structure using a scanning device. The condition of the structure can then be evaluated by comparing the map of regional decay constants with a map derived from a non-defective structure. According to the invention, there is no need to construct an estimate of the actual thermal properties of the sample, or to quantify the Kapitza resistance. Instead, using a pump-probe technique, a flag is raised by the simple detection of a variation from the expected behavior of the pump-probe system when applied to a specimen. The pump-probe system is adapted to permit very rapid data acquisition per pixel. Throughput is achieved by elimination of the steps required to characterize an anomaly in a specimen. It is sufficient to merely identify the presence of the anomaly for purposes of production line quality control.

The invention provides an optical apparatus for evaluating a sample, including beam processing optics for dividing a beam of pulsed coherent light into a pulsed pump beam and between one and three pulsed probe beams. The pump beam impinges on the sample for transient excitation thereof, and the probe beam impinges on the sample at a time subsequent to impingement thereon by the pump beam. The optical apparatus further includes a light detector disposed in a return path of the probe beam, and an analyzer that receives a signal from the detector that is responsive to light detected therein. An anomaly in the sample is indicated by a difference between returning light from the sample and returning light from a corresponding point in a reference sample. The analyzer may compute a time related function of the signal.

According to one aspect of the optical apparatus, the light detector is also disposed in a return path of the pump beam.

According to one aspect of the optical apparatus, the time related function is a first degree exponential decay curve.

According to another aspect of the optical apparatus, the analyzer further determines a decay constant of the curve.

According to a further aspect of the optical apparatus, responsively to the decay constant, the analyzer generates an indication of a sub-surface defect in the sample.

Yet another aspect of the optical apparatus includes a scanning mechanism for scanning the pump beam and the probe beam over the sample.

According to a further aspect of the optical apparatus, pulses of the coherent light have a duration between about 100 fsec and 3 psec.

According to still another aspect of the optical apparatus, pulses of the coherent light have a duration between about 100 fsec and 1 nsec.

According to yet another aspect of the optical apparatus, the pump beam is incident normal to a surface of the sample.

According to still another aspect of the optical apparatus, the pump beam is incident oblique to a surface of the sample.

According to yet another aspect of the optical apparatus, the beam processing optics process the pump beam and the probe beam by polarization.

According to still another aspect of the optical apparatus, the beam processing optics include a polarizing beamsplitter for dividing the beam into the probe beam and the pump beam, a retroreflector that reflects the probe beam, and a non-polarizing beam splitter receiving the probe beam via the retroreflector, and receiving the pump beam, for combining the probe beam and the pump beam.

According to an additional aspect of the optical apparatus, the beam processing optics process the pump beam and the probe beam by wavelength.

According to one aspect of the optical apparatus, the beam processing optics include a retroreflector that reflects the probe beam and a dichroic mirror for dividing the beam into the probe beam and the pump beam, and for recombining the probe beam and the pump beam.

According to another aspect of the optical apparatus, the beam processing optics also include a second harmonic generator crystal disposed in an optical path of the beam.

According to a further aspect of the optical apparatus, the probe beam includes a plurality of temporally dispersed beamlets, and the beam processing optics include a plurality of reflective edge filters disposed in a path of the beam, and a plurality of retroreflectors, each retroreflector reflecting one of the beamlets, and a dichroic mirror that receives the pump beam and the beamlets via the retroreflectors, and combines the beamlets with the pump beam.

According to an additional aspect of the optical apparatus, the beam processing optics include a pair of diffractive gratings disposed in a path of the beam for imposing a frequency chirp on pulses thereof.

According to one aspect of the optical apparatus, the probe beam includes a plurality of temporally dispersed beamlets, and the beam processing optics includes a plurality of reflective edge filters disposed in a path of the beam, and a plurality of retroreflectors, each of the retroreflectors reflecting one of the beamlets, and further includes focusing optics disposed in paths of the beamlets, wherein the beamlets impinge on the sample at different angles of incidence.

According to a further aspect of the optical apparatus, there is a first detector disposed within the specular angular range of the probe beam and a second detector disposed outside the specular angular range thereof.

According to another aspect of the optical apparatus, the polarization of the pump beam differs from the polarization of the probe beam, and there is a first detector disposed in a first return path of the pump beam from the sample, and a second detector disposed in a second return path of the probe beam from the sample, wherein a portion of the first return path avoids the second return path.

Yet another aspect of the optical apparatus includes a polarizing beamsplitter disposed in a common segment of the first return path and the second return path.

According to still another aspect of the optical apparatus, the polarizing beamsplitter is disposed within the specular angular range of the pump beam and within the specular angular range of the probe beam.

According to an additional aspect of the optical apparatus, the polarizing beamsplitter is disposed without the specular angular range of the pump beam and without the specular angular range of the probe beam.

In one aspect of the optical apparatus, there is a first probe beam and a second probe beam, the wavelength of the first probe beam differing from that of the second probe beam. The optical apparatus includes wavelength-responsive collection optics for the first probe beam and the second probe beam, the collection optics projecting the first probe beam in a first return path from the sample and projecting the second probe beam in a second return path from the sample. There is a first detector disposed in the first return path, and a second detector disposed in the second return path.

According to another aspect of the optical apparatus, a collection lens of the collection optics is disposed within the specular angular range of the first probe beam and within the specular angular range of the second probe beam.

According to a further aspect of the optical apparatus, a collection lens of the collection optics is disposed without the specular angular range of the first probe beam and without the specular angular range of the second probe beam.

In yet another aspect of the optical apparatus, the collection optics are disposed within a third return path from the sample of the pump beam, and includes a third detector disposed in the third return path.

According to still another aspect of the optical apparatus, the collection optics includes a plurality of reflective edge filters.

According to an additional aspect of the optical apparatus, the collection optics includes a prism.

According to one aspect of the optical apparatus, the collection optics includes a diffractive grating.

According to still another aspect of the optical apparatus, the probe beam includes a first probe beam and a second probe beam, the angle of incidence with the sample of the first probe beam differing from the angle of incidence with the sample of the second probe beam. The optical apparatus further includes first collection optics and second collection optics that respectively project the first probe beam in a first return path from the sample and the second probe beam in a second return path from the sample, and wherein the detector includes a first detector disposed in the first return path and a second detector disposed in the second return path.

According to yet another aspect of the optical apparatus, a collection lens of the first collection optics is disposed within the specular angular range of the first probe beam and a collection lens of the second collection optics is within the specular angular range of the second probe beam.

According to a further aspect of the optical apparatus, a collection lens of the first collection optics is disposed without the specular angular range of the first probe beam and a collection lens of the second collection optics is disposed without the specular angular range of the second probe beam.

According to another aspect of the optical apparatus, the detector also includes third collection optics that project the pump beam in a third return path from the sample, and includes a third detector disposed in the third return path.

The invention provides a method for evaluating a sample, which is carried out by impinging a pump beam of pulsed coherent light on the sample for transient excitation thereof, thereafter impinging a pulsed probe beam on an excited area of the sample, detecting returning light of the probe beam from the sample, comparing the returning light with corresponding returning light from a reference sample, and responsively to the comparison, indicating the presence of an anomaly in the sample. A time related function of the returning light may be computed.

Another aspect of the method includes processing the pump beam and the probe beam by polarization.

A further aspect of the method includes generating a source beam of pulsed coherent light, splitting the source beam to form the pump beam and the probe beam, polarizing the pump beam according to a first polarization, polarizing the probe beam according to a second polarization, projecting the pump beam along a first optical path that extends to the sample, and projecting the probe beam along a second optical path that extends to the sample, wherein the second optical path is longer than the first optical path.

Another aspect of the method includes processing the pump beam and the probe beam by wavelength.

In one aspect of the method the probe beam includes a plurality of temporally dispersed beamlets, which are impinged on the substrate by projecting the beamlets along optical paths, each of the paths extending to the sample, and each of the paths has a different length, wherein the beamlets impinge on the sample at different angles of incidence.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein:

FIG. 4 is a schematic illustration of an optical inspection system that is constructed and operative in accordance with an alternate embodiment of the invention, in which a pump beam and a probe beam differ in polarization;

FIG. 5 is a schematic illustration of an optical inspection system that is constructed and operative in accordance with an alternate embodiment of the invention, in which a probe beam is harmonically separated from a pump beam in frequency;

DETAILED DESCRIPTION OF THE INVENTION

Figure 1:
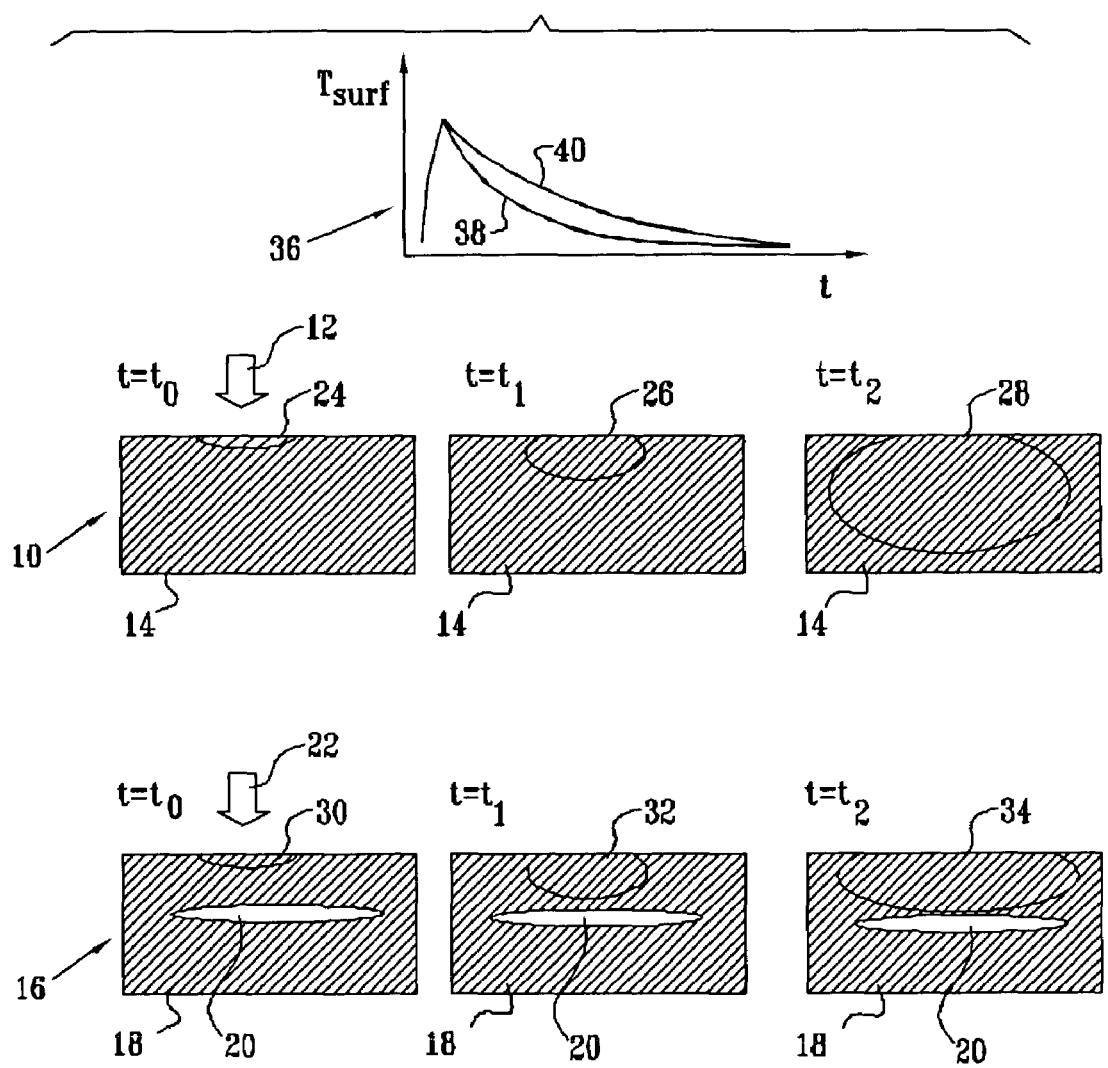
FIG. 1 is a composite illustration of the responses of a defective and a non-defective semiconductor structure following transient irradiation according to the present invention.

In the following description, numerous specific details are set forth in order to provide a thorough understanding of the present invention. It will be apparent to one skilled in the art, however, that the present invention may be practiced without these specific details. In other instances well-known circuits, and control logic have not been shown in detail in order not to unnecessarily obscure the present invention.

Overview.

By way of introduction, the inventors have discovered that heat dissipation in a non-homogeneous structure, such as an integrated circuit, is an extremely useful physical effect, which can be exploited in a particular way in order to detect buried defects. Because heat dissipation is a smooth function of time, only a very small number of timed measurements are required to analyze a signal. Indeed, in some applications of the present invention, an adequate analysis can be rapidly achieved using as few as 1–3 measurements. The initial form of the heating process is not important, as long as it occurs within a time interval that is short relative to the period of heat dissipation.

It has also been found that the transient response to heating is not very sensitive to initial conditions. Consequently, a single short pulse of a pump beamlet can be delivered with sufficient intensity for heat dissipation measurements, without recourse to averaging several pulses.

Surface heating induces both a reflectivity change and a surface deformation in a semiconductor substrate. In embodiments of the present invention, these two effects may be measured either simultaneously or individually in order to track the heat dissipation process. Measurement of specular reflection of a probe beamlet is especially useful for tracking reflectivity changes, and measurement of a deflected probe beamlet is especially useful for tracking surface deformation.

Heat dissipation causes the temperature of the sample to decay in an exponential fashion, which can be approximated by the equation $$T(t) = T_0 e^{-at}, \quad (1)$$

wherein T is temperature, $T_0$ is initial temperature, t is time, and a is a decay constant. The presence of various defects, such as voids and interface defects, generally slows the dissipation process, decreasing the value of the decay constant a. Assuming that the reflectivity or surface deformation is proportional to the temperature, the decay constant a may be estimated by measuring the reflected or scattered intensity of a probe beamlet at two or three points in time, and fitting a first degree exponential decay curve to the measurement data. The inventors have discovered that this estimate is practical, and that higher order effects may be ignored for purposes of quality control in a production environment.

Alternatively, it is practical to estimate the thermal decay using a simplified formula $$\alpha = \frac{\ln(T_2 - T_1)}{t_t - t_1}, \quad (2)$$

when there are only 2 or 3 measurements, for example one pump beamlet and only 1 or 2 probe beamlets.

Reference is now made to FIG. 1, which is a composite illustration of the responses to a pump beamlet of a defective and a non-defective semiconductor structure, each shown in cross-section. A top row 10 illustrates a thermal effect in response to an incident pump pulse 12 delivered at time $t_0$ upon a non-defective structure 14, which is shown at three different times. A bottom row 16 shows corresponding effects on a structure 18 having a subsurface void 20 that has been subjected to an identical pump pulse 22 delivered at time $t_0$. Ellipses 24, 26, 28 represent a front of heat energy that is dissipating within the structure 14. Ellipses 30, 32, 34 represent a corresponding front of heat energy in the structure 18. Generally, as the fronts progress through the structures 14, 18, the ellipses increase in area, and the heat energy that was imparted is distributed over an increasingly larger portion of the structures. Thus, for example in the structure 14, the ellipse 28 is larger in area than the ellipse 26. Consequently the average temperature of that portion of the structure 14 enclosed by the ellipse 28 is less than the average temperature of that portion of the structure 14 enclosed by the ellipse 26. Similarly, the ellipse 32 is larger than the ellipse 30, and the average temperature of that portion of the structure 18 enclosed by the ellipse 32 is less than the average temperature of that portion of the structure 18 enclosed by the ellipse 30.

Comparing corresponding ellipses in the top row 10 and the bottom row 16, initially there is no difference between the ellipse 24 and the ellipse 30 at time $t_0$, and there is only a small difference between the ellipse 26 and the ellipse 32 at time $t_1$. At time $t_2$, the ellipse 34 has a smaller area than the ellipse 28, and the local temperature of the portion of the structure 18 enclosed by the ellipse 34 is higher than the area of the structure 14 that is enclosed by the ellipse 28. This can be seen graphically in a plot 36, in which surface temperature $T_{SURF}$ is plotted against time, wherein a curve 38 and a curve 40 correspond to the structure 14 and the structure 18 respectively. The curves 38, 40 both decline exponentially according to Equation (1). It will be evident that the surface temperature of the defective structure 18 declines more slowly than that of the non-defective structure 14. The decay constant a (Eq. 1) of curve 40 is smaller than that of curve 38.

Using an inspection tool according to the present invention in a mass production environment, the precise location and character of defects need not always be ascertained. For some purposes of quality control, it is only necessary to flag the presence of a defect. In some embodiments, the presence of a defect may be determined by assigning a predetermined range of allowable values to the decay constant a, outside of which the sample is considered defective.

In some embodiments, suitable for patterned semiconductor wafers, values of the decay constant a (Eq. 1) in one sample are compared those obtained at corresponding locations of another sample. The values of the decay constant a (Eq. 1) may be combined with other aspects of optical signals described herein to improve throughput and otherwise facilitate determination of the presence of a defect, as is disclosed in commonly assigned application Ser. No. 10/097,442, entitled "Multi-Detector Defect Detection System and a Method for Detecting Defects", which is herein incorporated by reference. For instance, the intensity of the reflected pump beamlet can indicate whether or not the beamlet is currently incident on a metal surface or on a dielectric surface, the latter not being of interest in detecting voids. In some embodiments, reflectance information can be fed back to a scanner (not shown), which can then advance more rapidly in order in order to reach an area of greater interest.

In some embodiments the inventive techniques disclosed herein are combined in a more comprehensive system that is capable of inspecting an entire wafer, which includes subsystems that use conventional laser scattering detection arrangements. Such a comprehensive system is simultaneously capable of detecting surface defects, e.g., particles and scratches, as well as buried defects.

EMBODIMENT 1

Figure 2:
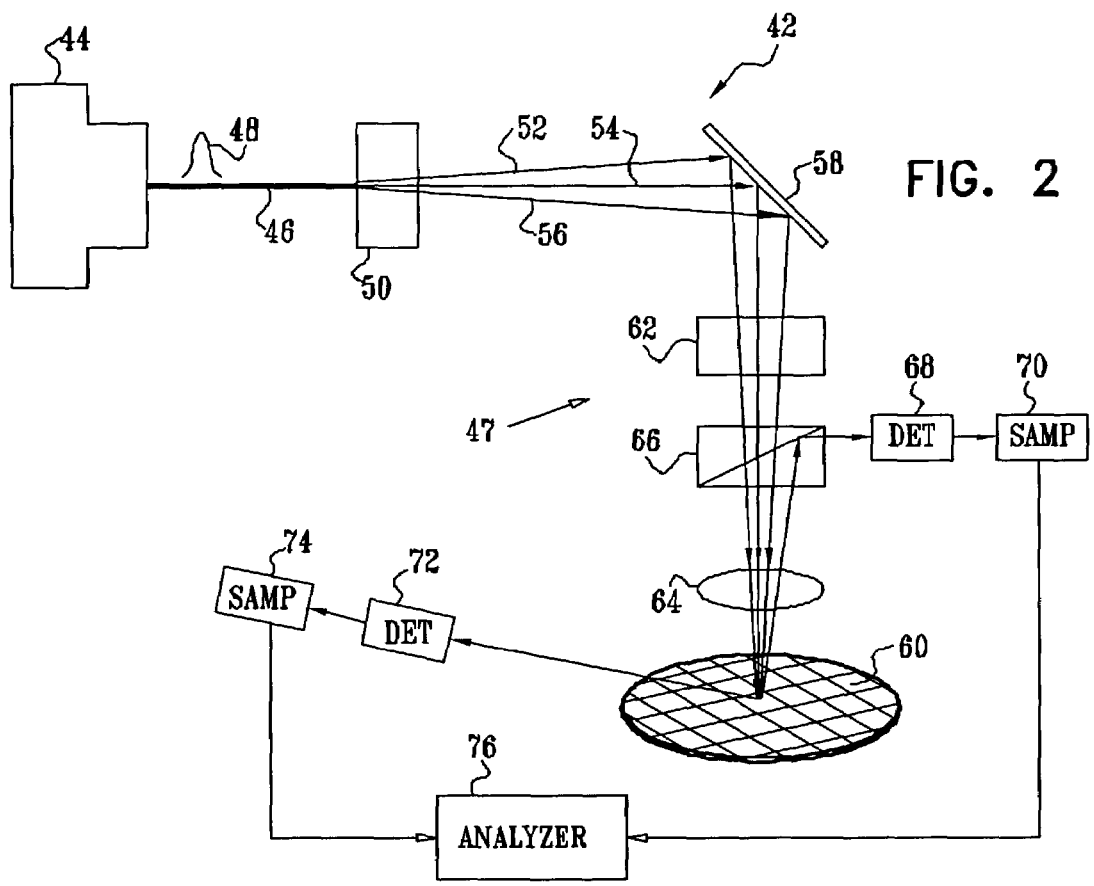
FIG. 2 is a high level schematic illustration of an optical inspection system that is constructed and operative in accordance with a disclosed embodiment of the invention.

Turning again to the drawings, reference is now made to FIG. 2, which is a high level schematic illustration of an optical inspection system 42 that is constructed and operative in accordance with a disclosed embodiment of the invention. FIG. 2 illustrates a number of features that are common to several other embodiments disclosed in further detail hereinbelow. The details of such common features are generally not repeated in the interest of brevity.

A modelocked laser source 44 emits a pulsed beam 46 of light, shown representatively as a pulse 48. The laser source 44 can, for example, be a Vitesse mode-locked Ti:sapphire laser, which produces 100 fsec pulses at a wavelength of 800 nm, or a DPM-1000 DPSS mode-locked Nd:YVO laser, which produces 3 psec pulses at a wavelength of 1047 nm. Both of these laser sources are available from Coherent Inc., 5100 Patrick Henry Drive, Santa Clara, Calif. 95054 USA. In some embodiments, the laser source 44 may produces pulses having a duration between about 100 fsec and 1 nsec. Alternatively, a source of pulsed non-coherent light can be used to produce the beam 46, except for embodiments having a DIC configuration.

The beam 46 enters beam processing optics 47, which includes a beam converter 50, which divides the beam 46 into a pump beamlet 52 and one or more probe beamlets, shown representatively as probe beamlets 54, 56. The beam converter 50 also delays the probe beamlets 54, 56 by different time intervals relative to the pump beamlet 52, and may further process the pump beamlet 52 and the probe beamlets 54, 56 so as to enable their discrimination by other characteristics. The beam processing optics 47 also include directing optics 58 and focusing optics 64.

The split of the beam 46 may be accomplished in some embodiments of the system 42 by varying the polarization of the beamlets. In such embodiments, there are only two distinct polarization states, so that only one pump beamlet and one probe beamlet are formed, for example the beamlet 54. This is done such that the polarization of the pump beamlet 52 differs from that of the beamlet 54. However, patterned metal interconnect layers in wafers typically have long, parallel conductors, which respond differently to orthogonal polarizations. When testing such structures, polarization dispersion may not be the best method for discriminating the pump beamlet 52 and the beamlet 54.

In other embodiments of the system 42 the pump beamlet 52 and the beamlets 54, 56 are processed according to wavelength. Short laser pulses from mode-locked lasers comprise a finite spectral range, so the different wavelengths may be selected from within the beam 46 itself. Alternatively, the beam 46 may undergo one or more nonlinear mixing processes, e.g., second and third harmonic generation, to produce a set of pulsed probe beamlets 54, 56, which are both completely synchronized with the pump beamlet 52, while the pump beamlet 52 and the probe beamlets 54, 56 are distinguished from one another in wavelength.

In yet other embodiments of the system 42, the directing optics 58 cause each of the pump beamlet 52 and the probe beamlets 54, 56 to impinge on a substrate 60 at a different angle. The probe beamlets 54, 56 are then discriminated using a plurality of detectors, each appropriately situated to collect the specular reflection of only one beamlet. This technique is suitable for detection of scattered light from surface deformations only if the deviation of the scattered light from the specular reflection angle is small.

In all embodiments of the system 42, the pump beamlet 52 and the probe beamlets 54, 56 are dispersed temporally, so that pulses therein each occupy a unique time subinterval of the interval between successive pulses emitted by the laser source 44. Following application of the pump beamlet 52, each of the probe beamlets 54, 56 is incident upon the substrate 60 at a different time. Exploitation of reflectance and scattering of the individual beamlets at the different times provides information about thermal decay in the substrate 60. The maximum time delay imparted to any of the probe beamlets 54, 56 must be less than the interval T between successive pulses of the beam 46 (and the pump beamlet 52), in order to maintain a causal relationship between each set of pump and probe pulses. The optimum interval between pulses of the beam 46 and the time delays of the probe beamlets 54, 56 are all application dependent, based on the composition of a particular substrate 60 under test. It is desirable that the interval between pulses of the beam 46 be at least 10 half lives of thermal decay, in order to assure that each succeeding pump beamlet arrives at a nearly fully relaxed surface. Furthermore, a scanner 62, used for scanning the beamlets over the substrate 60, is typically adjusted such that successive pump beamlets have some spatial overlap on the substrate 60. It is recommended that the overlap be substantial, or even complete. In any case, the area covered by the probe beamlets 54, 56 should not extend beyond the area covered by the pump beamlet 52. The time delays among the pump beamlet 52 and the probe beamlets 54, 56 are generally produced by sending each beamlet along an optical path of different length prior to directing it onto the wafer. Some well-known methods of optical delay are free-space delay paths, fiber-transmission path delays, and chirped pulse stretchers that employ a pair of diffraction gratings or prisms to impart a different delay time to different spectral components.

The pump beamlet 52 and the probe beamlets 54, 56 are displaced relative to the substrate 60 by the scanner 62 in order to inspect a given area of the substrate 60, and are impinged on the substrate 60 by directing optics 58 and focusing optics 64. The pump beamlet 52 and the probe beamlets 54, 56 can be impinged normal or oblique to the surface of the substrate 60.

The scanner 62, which can be any conventional optical deflection system, e.g., an oscillating mirror, rotating polygon mirror, or acousto-optic deflector, moves the pump beamlet 52 and the probe beamlets 54, 56 across the substrate 60 in a primary scanning direction. In some embodiments, the scanner 62 can be a 2-dimensional scanner, in which case the mechanical stage can be omitted. Additionally or alternatively, using conventional scanning techniques, many combinations of relative rotational and translational motion between the substrate 60 and the pump beamlet 52 and the probe beamlets 54, 56 may be employed in order to optimally scan different regions of the substrate 60. For example, the scanner 62 may be programmed to entirely skip regions of the substrate 60 in which defects can be well tolerated, or to sparsely sample different regions of the substrate 60 that are not too critical, while more essential areas are scanned exhaustively or even repetitively. Movement in a secondary scanning direction, which typically is orthogonal to the primary scanning direction, is typically achieved by mechanical displacement of the substrate 60 relative to the focusing optics 64. This can be accomplished by a suitable mechanical stage (not shown).

Light within the specular angular range of the pump beamlet 52 and the probe beamlets 54, 56 returns from the substrate 60 to collection optics 66 and is detected and processed by a detector 68 and a data sampler 70. Optionally, an additional detector 72 and a data sampler 74 may be provided for light that is scattered by the substrate 60.

The outputs of the data samplers 70, 74 are linked to a suitable analyzer 76, which approximates exponential curves to the detection information of the detectors 68, 72. The analyzer 76 may have multiple input channels, and can include output devices, such as displays or plotters (not shown) for displaying the curves and mapping local values of the decay constant a (Eq. 1) over the surface of the substrate 60. Such analyzers are well known in the art. For example, the data analysis hardware and software of the Compass™ wafer inspection system, available from Applied Materials, Inc. 3050 Bowers Avenue, Santa Clara, Calif. 95054, is suitable for the analyzer 76. It will be understood that in the detection schemes disclosed hereinbelow, in operation, the various detectors shown are coupled to the analyzer 76, typically via data samplers, although the details are generally omitted for clarity.

The profiles of the spot on the substrate 60 irradiated by the pump beamlet 52 and of the spots illuminated by the probe beamlets 54, 56 can have significant effect on the measurement. As has been disclosed with reference to FIG. 1, thermal diffusion following localized irradiation occurs both vertically and laterally. Buried voids and interfaces primarily affect vertical diffusion. Lateral diffusion of the heat actually reduces the effectiveness of the measurements made using the detector 68 and the detector 72. Since diffusion depends on the temperature gradient within the substrate 60, lateral diffusion can be minimized by configuring the pump beamlet 52 to irradiate a pump spot having a low lateral intensity gradient, e.g., a flat-top profile, in which a region containing at least 80% of the incident energy is uniform to within 5%. Lateral dissipation then occurs primarily at the edges of the pump spot. Thus, when attempting to detect subsurface voids, the focusing optics 64 are configured such that the spots illuminated by the probe beamlets 54, 56 be confined to a probe region that is smaller than the pump spot and centered therein. Vertical dissipation is the dominant effect seen in such a probe region. On the other hand, when attempting to detect surface deformations using scattered light from the probe beamlets 54, 56, then a flat-top profile of pump beamlet 52 may not be optimal, as a lateral thermal gradient is desirable in order to produce the required deformation.

In some embodiments of the system 42 surface deformation of the substrate 60 may also be detected using polarized pump-probe beamlets. The pump beamlet 52 and the probe beamlets 54, 56 are arranged in a differential interference contrast (DIC) configuration, in which case the laser source 44 must produce coherent light. The intensity and delay of the returning light pulses from the pump and probe beamlets (or two probe beamlets) of the same wavelength must be initially adjusted so that the two beamlets are approximately equal in amplitude, and overlap in time to intentionally create destructive interference when the beamlets impinge on a defect-free region of the substrate 60. The polarizations of the beamlets should also be rotated so that they match one another. The time delays are adjusted so that the beamlets produce nominal destructive interference, in order to provide a zero-background signal. The detector signals corresponding to each of the probe beamlets then constitute an interferometric measurement of the displacement of the surface substrate 60 relative to its position at the initial time $t_0$, when the pump beamlet was incident. As thermal relaxation occurs over time, the relative surface displacement approaches zero exponentially.

Figure 3:
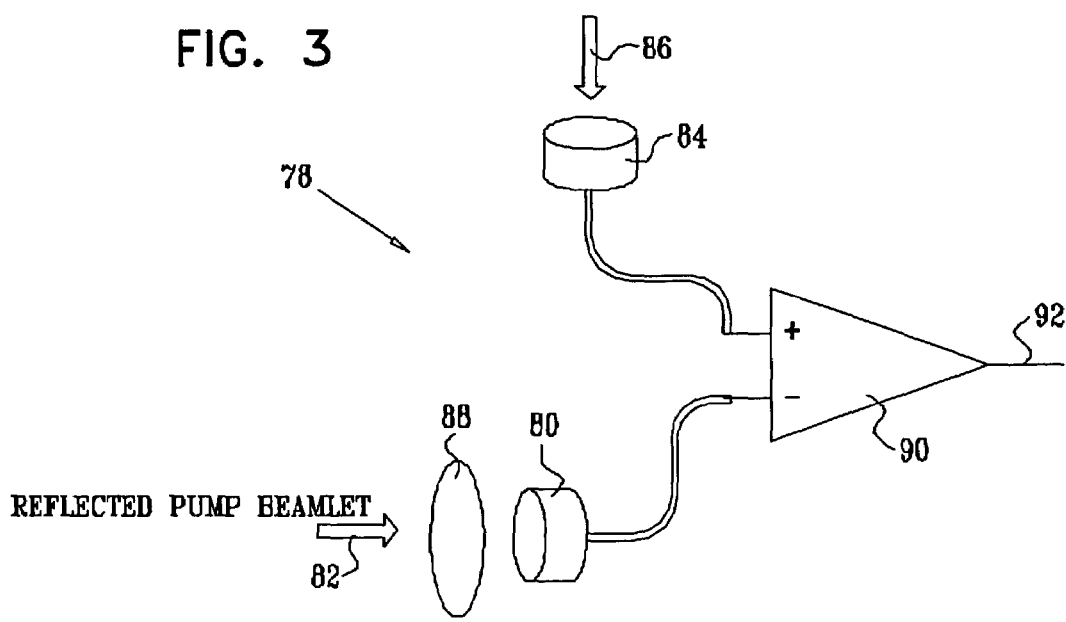
FIG. 3 is a schematic diagram of a photodetector circuit suitable for use in detectors of the optical inspection system shown in FIG. 2 in accordance with a disclosed embodiment of the invention.

It is desirable to provide a balanced photodetector arrangement for the detectors in the system 42, in order to reduce a large DC offset and improve the SNR. Reference is now made to FIG. 3, which is a schematic diagram of a photodetector circuit 78 suitable for use in the detectors 68, 72 in accordance with a disclosed embodiment of the invention. A photodetector 80 receives a reflected pump beamlet 82, and a photodetector 84 receives a reflected probe beamlet 86. A variable attenuator 88 is placed in the path of one of the pump beamlet 82 and the probe beamlet 86 in order to equalize the signal outputs of the photodetectors 80, 84. In general, the pump beamlet 82 and the probe beamlet 86 are separated in time by a delay $t_{delay}$, which is short relative to the detector bandwidth, such that the detector is insensitive to this time delay. The outputs of the photodetectors 80, 84 are fed into a differential amplifier 90, which produces an output signal on line 92 that represents the difference of the outputs of the photodetectors 80, 84. To calibrate the circuit 78, the delay $t_{delay}$ is set to 0, and the variable attenuator 88 is adjusted so as to null the output of the differential amplifier 90. A model 1807 balanced photoreceiver, available from New Focus, Inc., 2584 Junction Avenue. San Jose, Calif. 95134, can be used in the detectors 68, 72 to accomplish the objectives of the circuit 78.

EMBODIMENT 2

Reference is now made to FIG. 4, which is a schematic illustration of an optical inspection system 94 that is constructed and operative in accordance with an alternate embodiment of the invention. A modelocked laser source 96 emits a variably polarized output beam 98 having a desired ratio of output intensities, as explained hereinbelow. Alternatively, a source of pulsed non-coherent light can be used to produce the beam 98, except for embodiments having a DIC configuration. The beam 98 is split by a polarizing beamsplitter 100 into a pump beamlet 102 and a probe beamlet 104. The ratio of the intensity of the pump beamlet 102 to that of the probe beamlet 104 can be adjusted by adjusting the polarization of the beam 98. The pump beamlet 102 enters a non-polarizing beamsplitter 106, passes through the focusing optics 64, and impinges on the substrate 60. The pump beamlet 102 can impinge normally or obliquely on the substrate 60. The probe beamlet 104 passes through a retroreflector 108, and is reflected towards the beamsplitter 106 by a reflector 110. The retroreflector 108 is adjustable to provide a path varying in length, and thus a variable time delay, for the probe beamlet 104 relative to the pump beamlet 102. The pump beamlet 102 and the probe beamlet 104 are realigned in the beamsplitter 106 to follow a substantially common path 112, which passes through the focusing optics 64, and impinges on the substrate 60. The common path 112 can impinge normally or obliquely on the surface of the substrate 60, and the pump beamlet 102 may be offset from the probe beamlet 104.

In the system 94, the beamsplitter 100 and the retroreflector 108 constitute a beam converter, processing the beam 98 both by polarization and by time delay. The detection scheme for the system 94 can be any of the detection schemes disclosed hereinbelow.

EMBODIMENT 3

Reference is now made to FIG. 5, which is a schematic illustration of an optical inspection system 114 that is constructed and operative in accordance with an alternate embodiment of the invention. Many details of the system 114 that are identical in the system 94 (FIG. 4) are not repeated in the interest of brevity. In the system 114, the pulse 48 undergoes harmonic generation, to produce a set of probe pulses, which are completely synchronized with the pump pulse and distinguished from it in wavelength. The beam 46 passes through a second harmonic generator (SHG) crystal 116. An emerging beam 118 thus has two distinct, harmonically related frequency components. The beam 118 is split by a dichroic mirror 120 into a pump beamlet 122 and a probe beamlet 124, the probe beamlet 124 having a frequency, which is the second harmonic of the pump beamlet 122. Alternatively, the pump beamlet 122 may be the second harmonic of the probe beamlet 124. The probe beamlet 124 is redirected by the retroreflector 108 and the reflector 110. The pump beamlet 122 enters another dichroic mirror 126, where it is realigned with the probe beamlet 124 to follow a substantially common path 128, which passes through the focusing optics 64, and impinges on the substrate 60. The common path 128 can be normal or oblique to the surface of the substrate 60, and the pump and probe components may be offset from one another.

In the system 114, the crystal 116, dichroic mirror 120, and retroreflector 108 constitute a beam converter, processing the pump beamlet 122 and the probe beamlet 124 both by wavelength and by time delay. The detection scheme for the system 114 can be any of the detection schemes disclosed herein.

In some embodiments, the crystal 116 can be realized by a crystal for generating third harmonics. Additionally or alternatively, the crystal 116 can be realized by a plurality of harmonic generation crystals, each in its own optical path, so that a plurality of wavelength-dispersed probe beamlets can be produced.

EMBODIMENT 4

Figure 6:
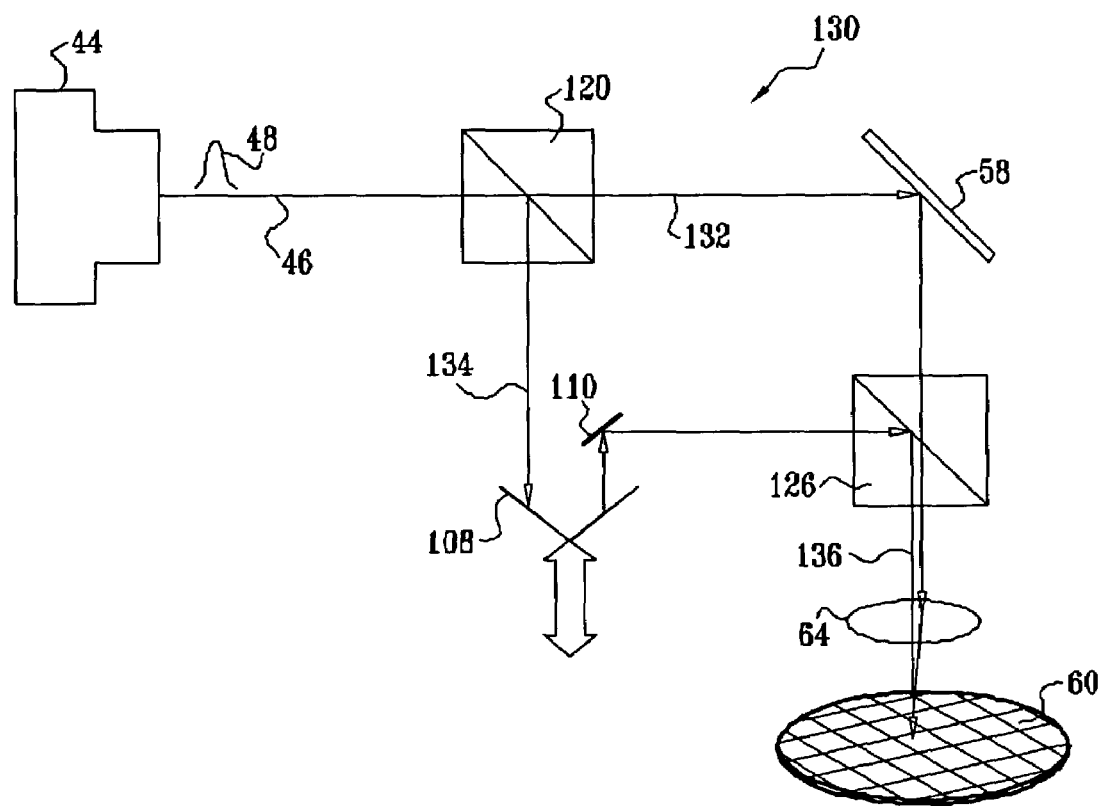
FIG. 6 is a schematic illustration of an optical inspection system that is constructed and operative in accordance with an alternate embodiment of the invention, in which a probe beam and a pump beam are divided according to wavelength using a dichroic mirror, and temporally dispersed using a retroreflector.

Reference is now made to FIG. 6, which is a schematic illustration of an optical inspection system 130 that is constructed and operative in accordance with an alternate embodiment of the invention. The system 130 is similar to the system 114 (FIG. 5), except that the crystal 116 is omitted.

The system 130 exploits the fact that the ultrafast pulse 48 inherently contains a large spectral bandwidth, with a minimum bandwidth $\Delta\omega$ given by: $\Delta\omega\cdot\tau\cong 1$. The beam 46 is split by the dichroic mirror 120 into a pump beamlet 132 and a probe beamlet 134, the pump beamlet 132 having different frequency components from the probe beamlet 134. The probe beamlet 134 is redirected by the retroreflector 108 and the reflector 110. The pump beamlet 132 enters another dichroic mirror 126, where it is realigned with the probe beamlet 134 to follow a substantially common path 136, which passes through the focusing optics 64, and impinges on the substrate 60. The common path 136 can impinge normally or obliquely on the surface of the substrate 60, and the pump beamlet 132 may be offset from the probe beamlet 134.

In the system 130, the dichroic mirror 120 and the retroreflector 108 constitute a beam converter, processing the pump beamlet 132 and the probe beamlet 134 both by wavelength and by time delay. The detection scheme for the system 114 can be any of the detection schemes disclosed herein.

EMBODIMENT 5

Figure 7:
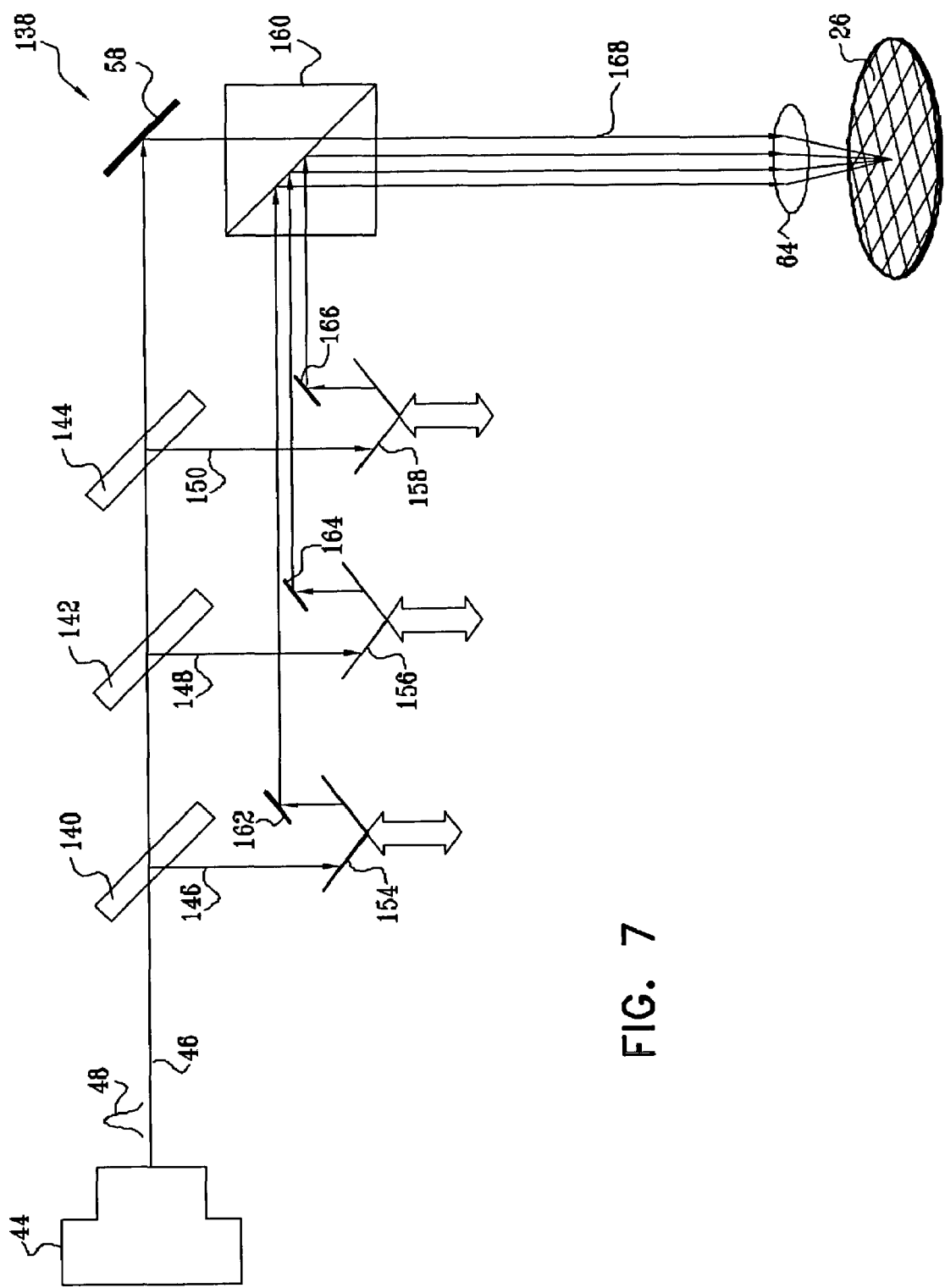
FIG. 7 is a schematic illustration of an optical inspection system that is constructed and operative in accordance with an alternate embodiment of the invention, in which pump and probe beams are processed temporally and by wavelength using a series of reflective edge filters and retroreflectors.

Reference is now made to FIG. 7, which is a schematic illustration of an optical inspection system 138 that is constructed and operative in accordance with an alternate embodiment of the invention. In the system 138 a series of reflective edge filters 140, 142, 144 receives the beam 46, and produces multiple beamlets 146, 148, 150, and a pump beamlet 152, each having a unique waveband. The beamlets 146, 148, 150 are received respectively by retroreflectors 154, 156, 158. The beamlets 146, 148, 150 are then directed to a dichroic mirror 160 by reflectors 162, 164, 166, where they are realigned with the pump beamlet 152 to follow a substantially common path 168.

The retroreflectors 154, 156, 158 form free-space delay lines. They are disposed so that the optical paths of the beamlets 146, 148, 150, and the pump beamlet 152 are all of different lengths. Thus, the reflective edge filters 140, 142, 144 and the retroreflectors 154, 156, 158 cooperate to constitute both a temporal and wavelength beam converter for the beam 46.

The common path 168 passes through focusing optics 64, and impinges on the substrate 60, each component arriving at a different time. The common path 168 can be normal or oblique to the surface of the substrate 60, and the pump and probe components may be offset from one another. The detection scheme for the system 114 can be any of the detection schemes disclosed herein.

EMBODIMENT 6

Figure 8:
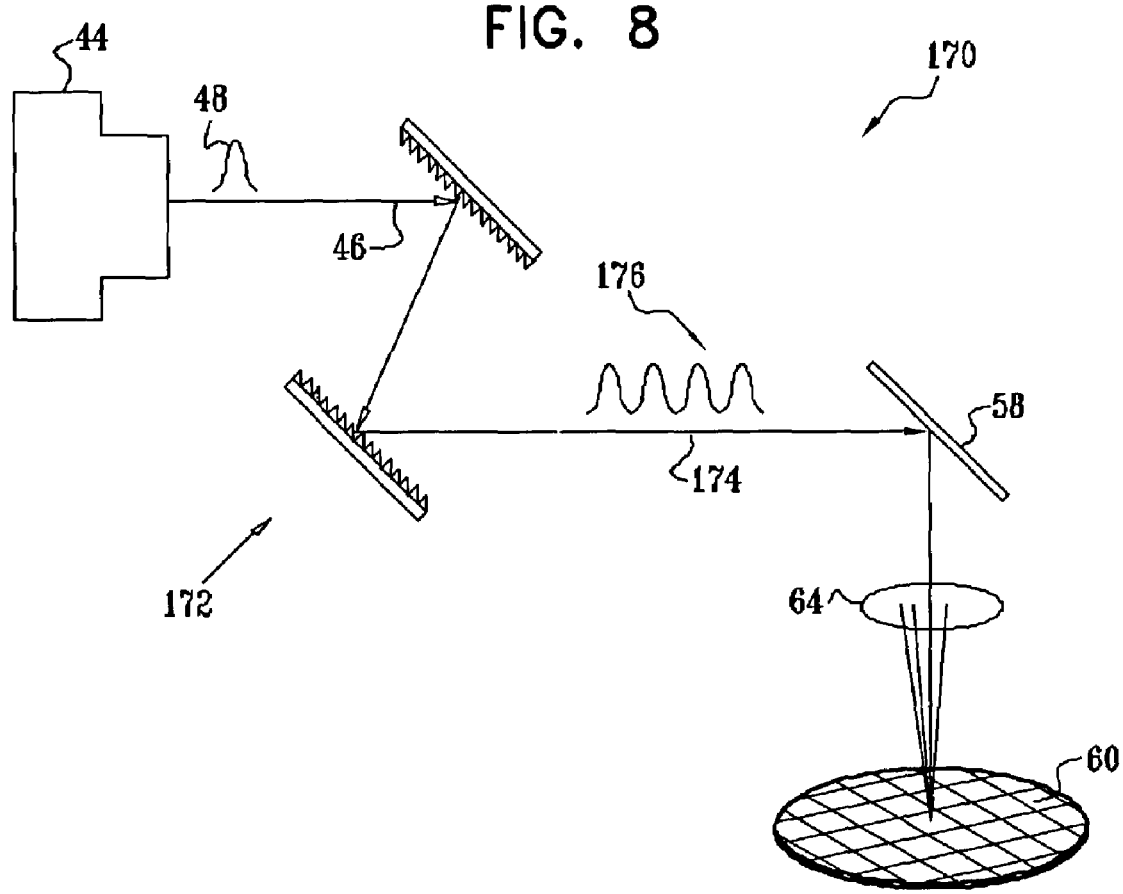
FIG. 8 is a schematic illustration of an optical inspection system that is constructed and operative in accordance with an alternate embodiment of the invention, in which pump and probe beams are processed temporally and by wavelength using a diffractive grating pair.

Reference is now made to FIG. 8, which is a schematic illustration of an optical inspection system 170 that is constructed and operative in accordance with an alternate embodiment of the invention. In the system 170, a parallel diffractive grating pair 172 is introduced into the path of the beam 46. The grating pair 172 introduces a group delay, stretching the pulse 48, to produce a frequency-chirped beam 174. The grating pair 172 is configured by choosing the distance between the pair, the incidence angle of the beam 46, and the grating period in a known manner, so as to spread the pulse across all or part of the time interval between successive pulses emitted by the laser source 44. The beam 174 actually consists of a train of pulses 176, all occurring within the time interval T.

In the system 170, the grating pair 172 constitutes a beam converter, processing the beam 46 both by wavelength and by time delay. Alternatively, a prism pair may be used for this same purpose, as is known in the art. The detection scheme for the system 170 can be any of the detection schemes disclosed herein.

Figure 9:
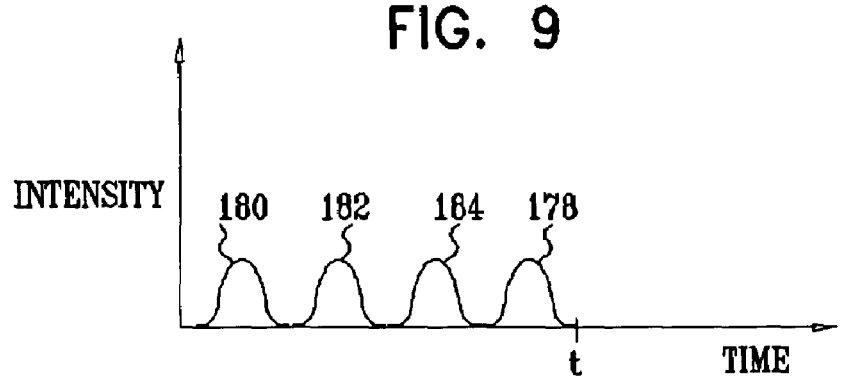
FIG. 9 is a composite plot illustrating temporal dispersion of the pulse generated in the system shown in FIG. 8.

Reference is now made to FIG. 9, which is a composite plot illustrating temporal dispersion of the pulse 48 (FIG. 8). A peak 178, which represents the first pulse in the train of pulses 176 (FIG. 8), is a pump pulse. Succeeding peaks 180, 182, 184 correspond to probe pulses. Each of the peaks 178, 180, 182, 184 has a different waveband, and is delayed differently from the others.

EMBODIMENT 7

Figure 10:
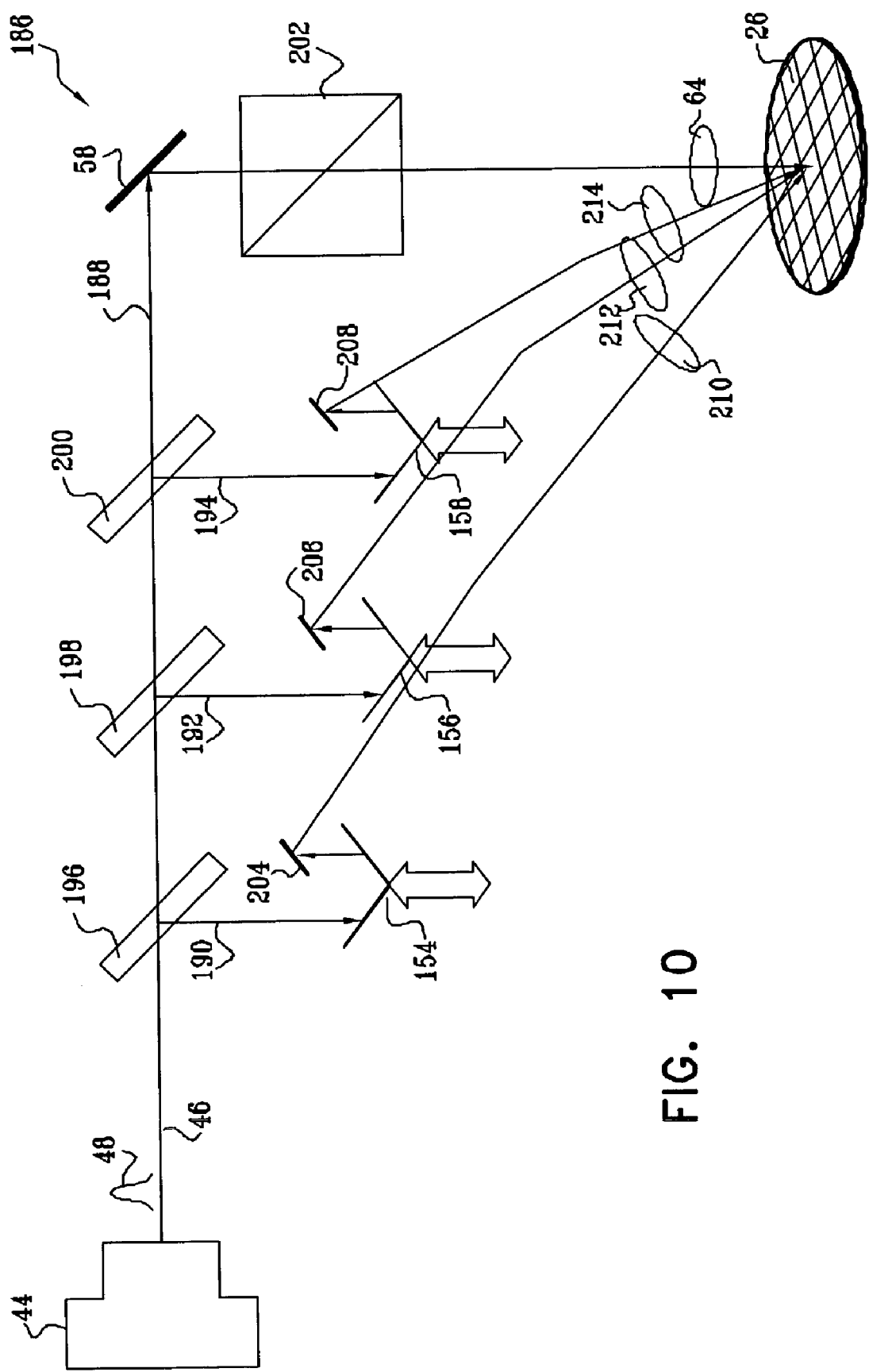
FIG. 10 is a schematic illustration of an optical inspection system that is constructed and operative in accordance with an alternate embodiment of the invention, in which a plurality of temporally dispersed probe beams impinge a substrate at different angles.

Reference is now made to FIG. 10, which is a schematic illustration of an optical inspection system 186 that is constructed and operative in accordance with an alternate embodiment of the invention. In this embodiment, the beam 46 is split into a pump beamlet 188, and a plurality of probe beamlets 190, 192, 194 by beamsplitters 196, 198, 200, respectively. The pump beamlet 188 is directed by the directing optics 58 through a beamsplitter 202 and focusing optics 64, and impinges on the substrate 60 either normally or obliquely.

The relative reflectance and transmittance of each of the beamsplitters 196, 198, 200 are typically (but not necessarily) chosen so that all the beamlets 190, 192, 194 have equal intensities. The beamlets 190, 192, 194 are retroreflected respectively by retroreflectors 154, 156, 158. The beamlets 190, 192, 194 are then redirected by reflectors 204, 206, 208 generally toward the substrate 60 through focusing optics 210, 212, 214, respectively. The reflectors 204, 206, 208 are arranged so as to impinge the beamlets 190, 192, 194 on the substrate 60 at different angles. The spots illuminated by the beamlets 190, 192, 194 and the pump beamlet 188 may be coincident, or offset from one another in many different combinations.

The retroreflectors 154, 156, 158 form free-space delay lines. They are disposed so that the optical paths of the beamlets 190, 192, 194 are of different lengths. Thus, the beamsplitters 196, 198, 200, the retroreflectors 154, 156, 158, and the reflectors 204, 206, 208 cooperate to constitute a temporal beam converter for the beam 46. The detection scheme for the system 186 can be any of the detection schemes disclosed herein. An advantage of the embodiment represented by the system 186 is that it does not require multiple wavelengths for the beamlets 190, 192, 194. Thus, a narrow-spectrum laser can be used as the laser source 44. Furthermore, there is good physical separation between the reflected beamlets, eliminating possible crosstalk in collinear embodiments. In some applications, crosstalk can be even further reduced by using combinations of angular and spectral separation of the beamlets 190, 192, 194.

EMBODIMENT 8

Figure 11:
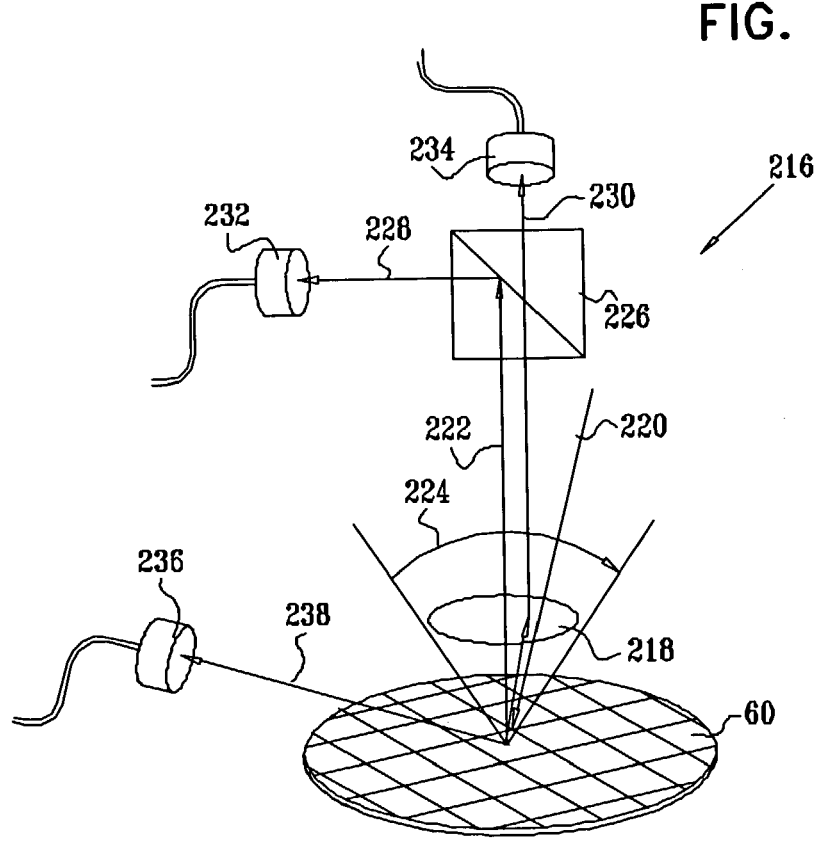
FIG. 11 is a schematic illustration of a detection subsystem that detects reflected light, for use in embodiments of the invention in which pump and probe beams are processed according to polarization.

Reference is now made to FIG. 11, which is a schematic illustration of a detection subsystem 216 that is constructed and operative for use in alternate embodiments of the invention. The subsystem 216 is particularly useful in embodiments of the invention in which the pump and probe beamlets are processed according to polarization, for example the system 94 (FIG. 4). The subsystem 216 is described with reference to FIG. 4 by way of example, it being understood that the disclosure is applicable to other embodiments herein.

Beam collecting optics 218 are mounted within the specular angular range of pump and probe beamlets 220, for example the probe beamlet 104 (FIG. 4), to capture a reflected beam 222 from the pump and probe beamlets that return from the substrate 60. The specular angular range is represented by an angle 224, The collecting optics 218 may be the same as or different from the focusing optics 64 (FIG. 4). The beam 222 enters a polarizing beamsplitter 226, where it is divided into a probe beamlet 228 and a pump beamlet 230, which are detected respectively by a probe detector 232 and a pump detector 234. As noted above, the probe detector 232 and pump detector 234 may be fast single element detectors or fast imaging detectors. The purpose of collecting information from the pump detector 234 regarding the pump beamlet 230 is to establish baseline conditions at time t=0. The pump detector 234 sees the substrate during the initial rise in temperature, and also provides a reference for the probes, compensating for variations between different specimens due to surface roughness, line width, precise position over the pattern, etc. These physical characteristics can cause variations in the signals, which are unrelated to thermal effects. These effects can be eliminated by dividing probe signals by pump signals to produced normalized signals. Furthermore, as discussed above, the signals due to temperature changes are relatively small and are carried on a larger DC signal. The DC component from the pump beamlet 230 can be subtracted from the probe beamlet 228 using balanced photodetectors as disclosed above with respect to Embodiment 1. The probe detector 232 collects information at different points during the time interval T to establish the decay constant a (Eq. 1) that applies to the region of the substrate 60 currently being illuminated.

A detector 236 is disposed outside the angle 224 and detects scattered light from the pump beamlet and the probe beamlets. A fast single element detector can be used as the detector 236. Alternatively, the detector 236 can be realized by multiple detectors, disposed at different points surrounding the point of illumination. The detector 236 should be as far as possible outside the specular angle. Optimally the angle included by the incident beam and a ray 238 leading from the substrate 60 to the detector 236 should be 90 degrees. Smaller angles are also useful, but the angle between the incident beam and the ray 238 should be at least twice as large as the NA of the illumination optics, that is the half-angle of the illumination cone.

EMBODIMENT 9

Figure 12:
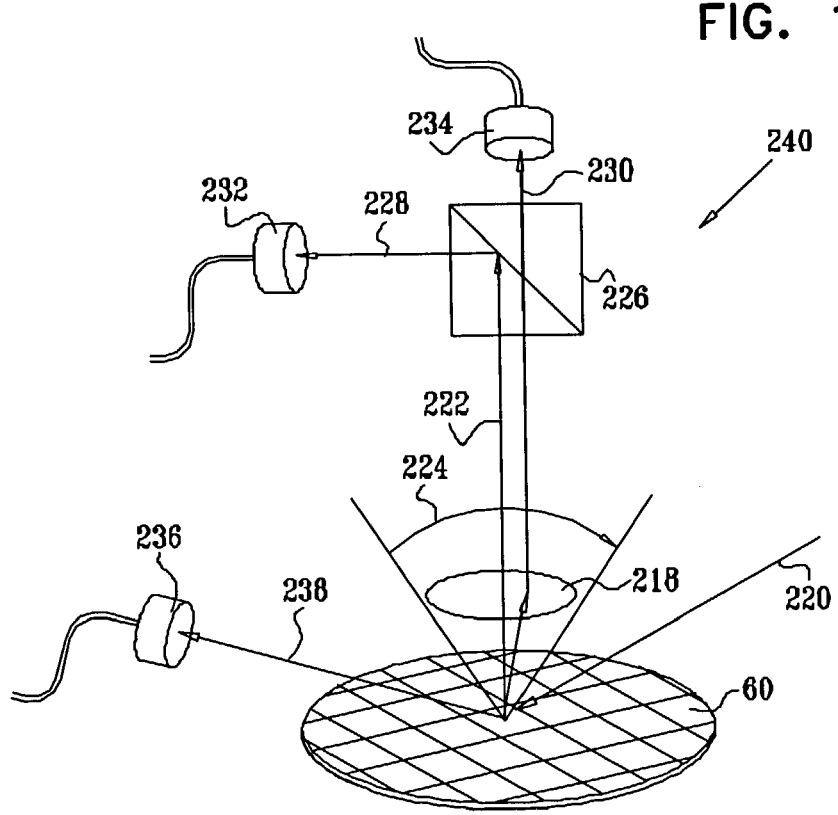
FIG. 12 is a schematic illustration of a detection subsystem that detects scattered light, for use in embodiments of the invention in which pump and probe beams are processed according to polarization.

Reference is now made to FIG. 12, which is a schematic illustration of a detection subsystem 240 that is constructed and operative for use in alternate embodiments of the invention. The subsystem 240 is similar to the subsystem 216 (FIG. 11). However, in the subsystem 240 the pump and probe beamlets 220 arrive at the substrate 60 from a direction that is outside the angle 224. Now the probe detector 232 and the pump detector 234 detect scattered rather than reflected light. An additional detector 236 may be used to detect scattered light from the pump and/or probe beamlets. The probe detector 232 and the pump detector 234 should collect light within the cone of specularly reflected light but should be de-centered. For example, using an illumination cone of ±10 degrees from the normal direction, the collection optics should collect an angle of ±2 degrees, centered at 2 degrees to one side of the normal angle. The probe beamlet also be displaced to one side of the pump beamlet by about half the beamlet diameter, so as to receive a well-defined deflection caused by surface distortion. In this embodiment, the pump and probe beamlets do not fully overlap.

EMBODIMENT 10

Figure 13:
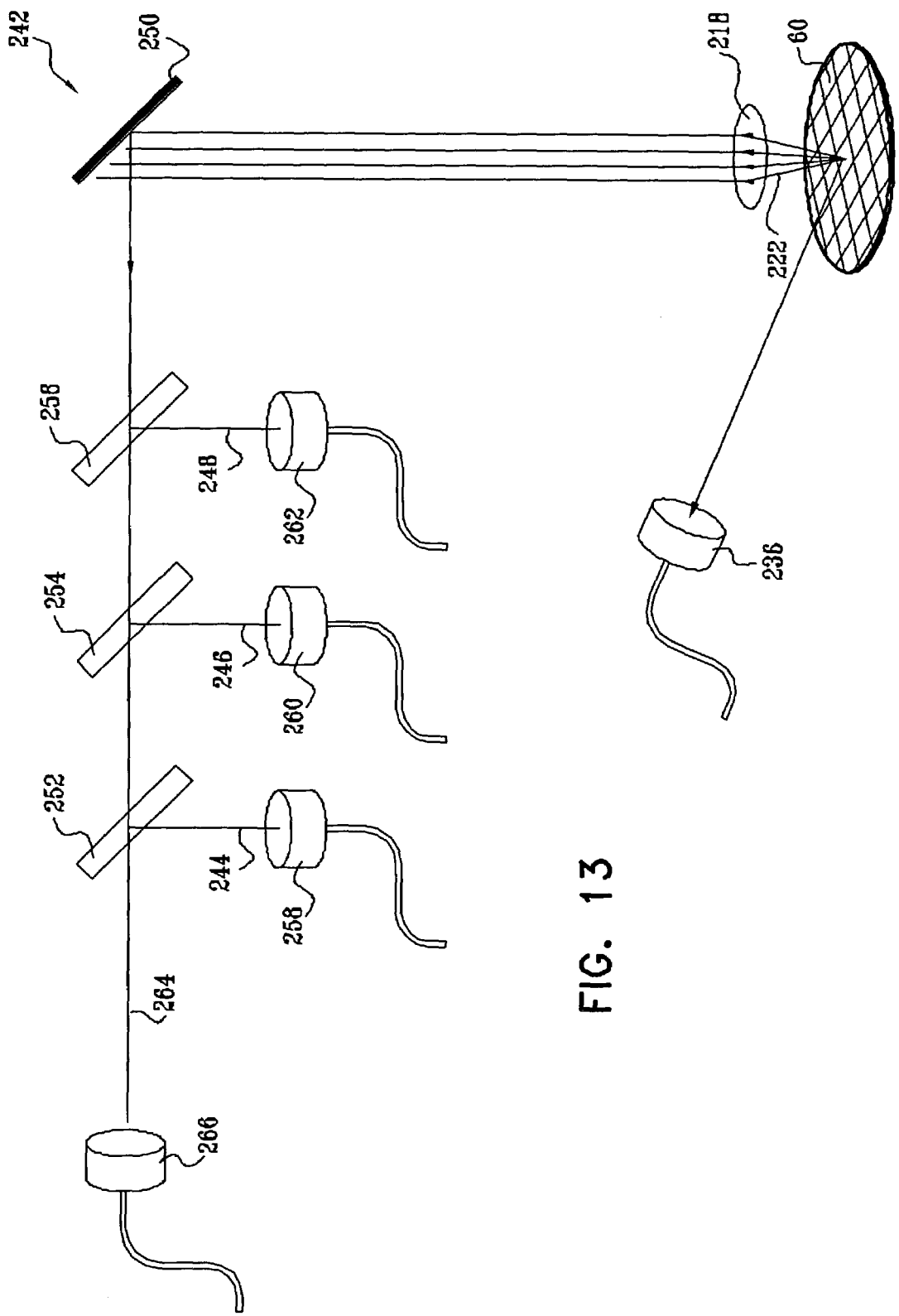
FIG. 13 is a schematic illustration of a detection subsystem employing a series of edge filters that is constructed and operative for use in embodiments of the invention in which a plurality of probe beams differ in wavelength.

Reference is now made to FIG. 13, which is a schematic illustration of a detection subsystem 242 that is constructed and operative for use in alternate embodiments of the invention. The subsystem 242 is particularly useful in those embodiments in which the probe beamlets have been processed by wavelength, for example the system 114 (FIG. 5).

The beam 222 that is reflected or scattered from the substrate 60 passes through collecting optics 218. Probe beamlets 244, 246, 248, which are components of the beam 222, and which have different wavebands, are redirected by a reflector 250 through a series of reflective edge filters 252, 254, 256 to corresponding probe detectors 258, 260, 262. The edge filters 252, 254, 256 are each configured to redirect one of the probe beamlets 244, 246, 248, and to allow the other probe beamlets to continue onward. A pump beamlet 264, which is another component of the beam 222, passes through all of the edge filters 252, 254, 256, and continues toward a pump detector 266. Because the probe beamlet components of the beam 222 are pre-sorted by the edge filters 252, 254, 256, the detectors 258, 260, 262 are not required to be waveband selective.

In the subsystem 242 the collecting optics 218 may be located within or without the specular angular range of the incident pump and probe beamlets (not shown). In the latter case, the detector 236 may be omitted if desired, or it may be used to collect specularly reflected radiation, as the detectors 258, 260, 262, 266 already function as dark-field detectors.

EMBODIMENT 11

Figure 14:
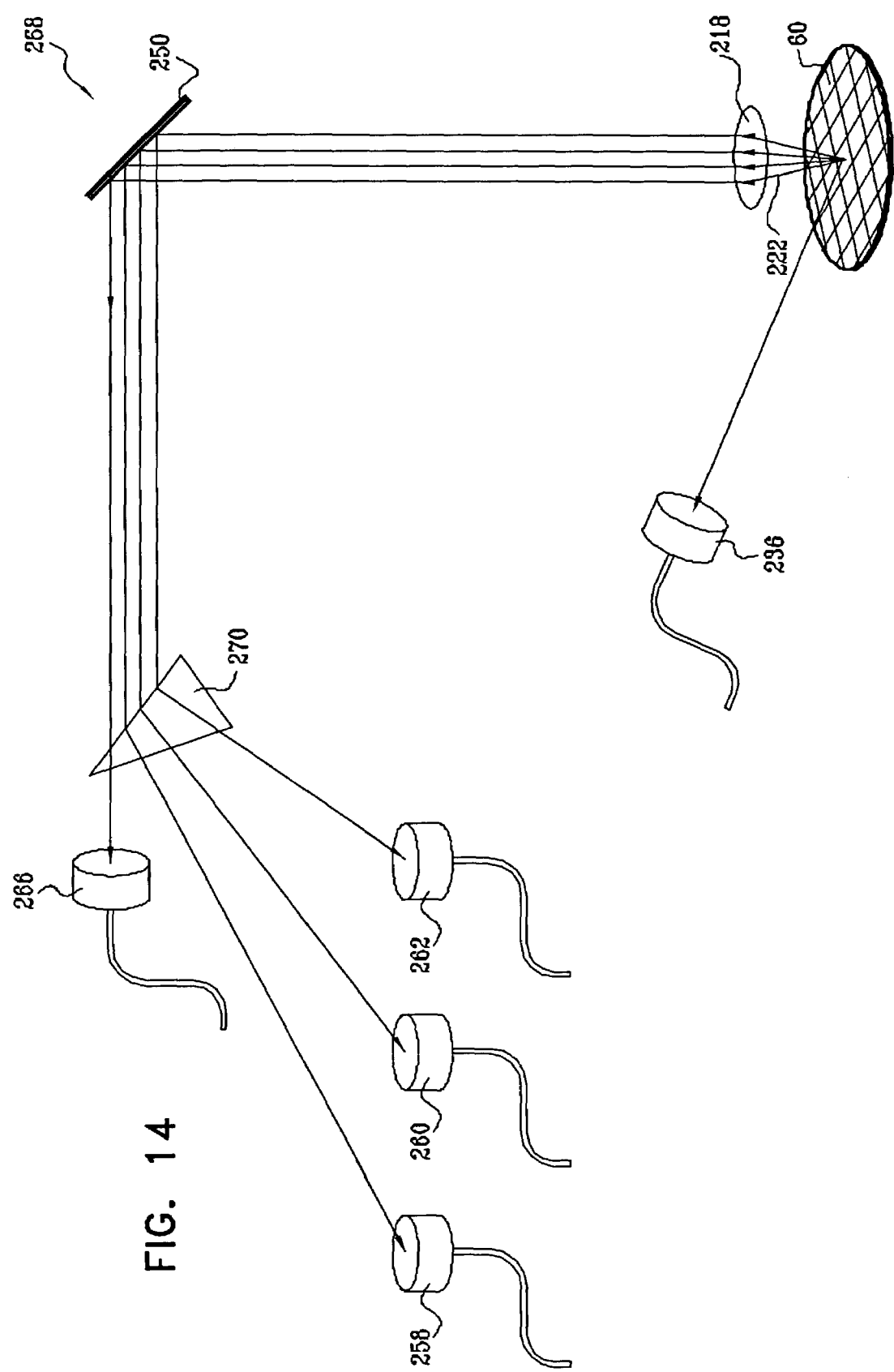
FIG. 14 is a schematic illustration of an alternate detection subsystem employing a prism that is constructed and operative for use in embodiments of the invention in which a plurality of probe beams differ in wavelength.

Reference is now made to FIG. 14, which is a schematic illustration of a detection subsystem 268 that is constructed and operative for use in alternate embodiments of the invention. The subsystem 268 is similar to the subsystem 242 (FIG. 13), and provides wavelength dispersion of the beam 222. However in the subsystem 268, this is achieved using a prism 270, in place of the edge filters 252, 254, 256 (FIG. 13). Other dispersive elements, as are known in the art, such as a grating, may be used in place of the prism 270.

In the subsystem 268, the collecting optics 218 may be located within or without the specular angular range of the incident pump and probe beamlets (not shown). In the latter case, the detector 236 may be used to collect specularly reflected radiation, as the detectors 258, 260, 262, 266 already function as dark-field detectors.

EMBODIMENT 12

Figure 15:
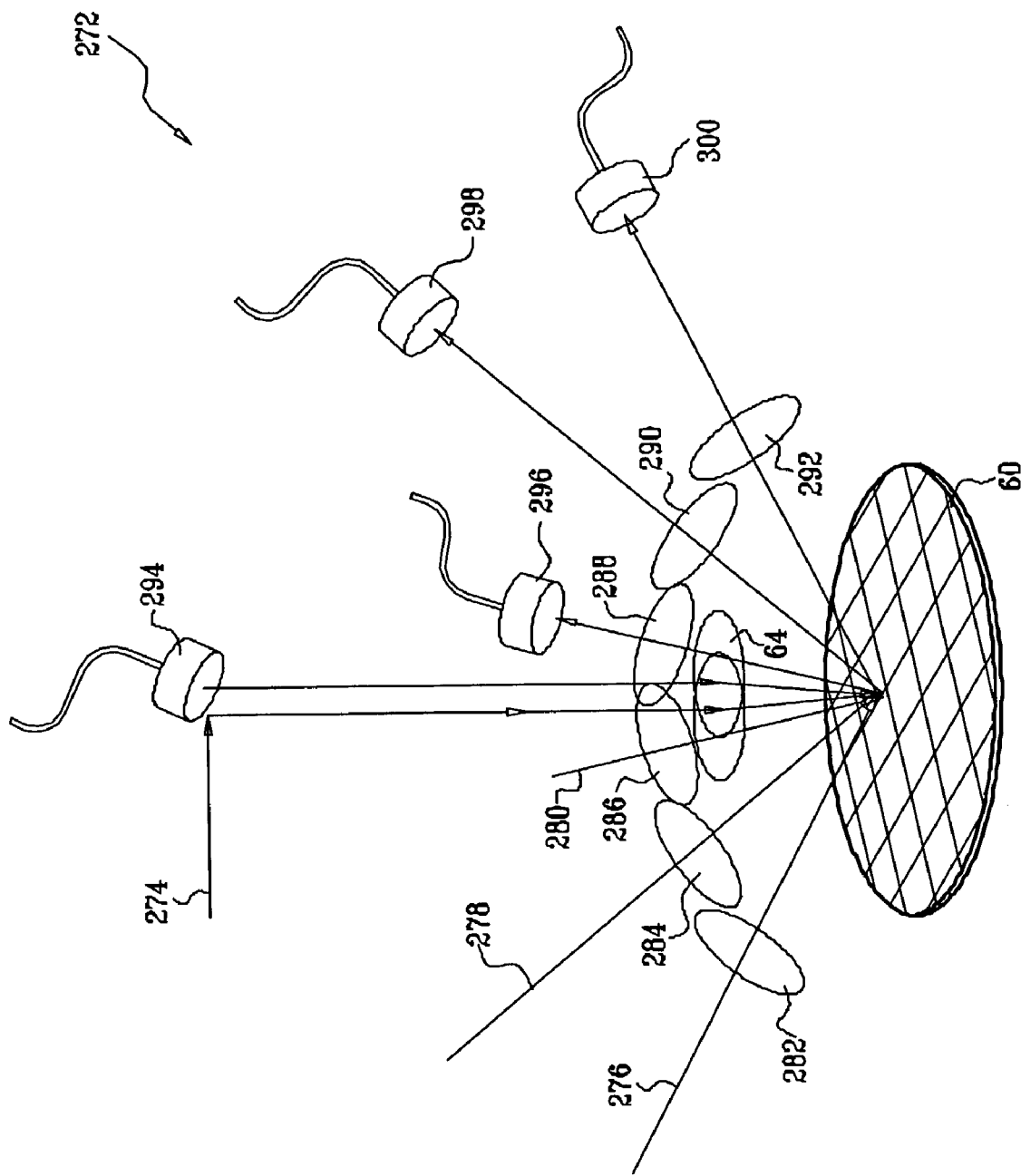
FIG. 15 is a schematic illustration of a detection subsystem that is constructed and operative for use in embodiments of the invention in which a plurality of probe beams impinge a substrate at different angles of incidence.

Reference is now made to FIG. 15, which is a schematic illustration of a detection subsystem 272 that is constructed and operative for use in alternate embodiments of the invention. In the subsystem 272, a pump beamlet 274 reaches the substrate 60 via focusing optics 64. The pump beamlet 274 can be generated using any of the embodiments disclosed herein, and can impinge normally or obliquely on the surface of the substrate 60. A plurality of probe beamlets 276, 278, 280 are directed to the substrate 60 by respective focusing optics 282, 284, 286. The probe beamlets 276, 278, 280 may be generated by any of the embodiments disclosed herein that result in spatial separation of a plurality of probe beamlets. For example, the system 186 (FIG. 10) would be suitable. Alternatively, the probe beamlets 276, 278, 280 may be generated using any other method of generating a plurality of pulsed beams. It should be noted that the subsystem 272 is not suitable for DIC configuration.

The spots on the substrate 60 that are illuminated by the probe beamlets 276, 278, 280 may coincide with the spot illuminated by the subsystem 272, or be offset from one another in many different combinations. In any case, the angles of incidence of the probe beamlets 276, 278, 280 with the substrate 60 are different. The angles of reflection of the probe beamlets 276, 278, 280 are therefore correspondingly different at a given point on the detectors 258, 260, 262.

Reflected light from the probe beamlets 276, 278, 280 passes respectively through collecting optics 288, 290 292. The reflection of the pump beamlet 274 returns via the focusing optics 64. In some embodiments separate collection optics (not shown) could be included in the path of the reflection of the pump beamlet 274. Each of the collecting optics 288, 290 292 are located outside the specular angular range of all the probe beamlets 276, 278, 280 other than its respective probe beamlet.

The reflection of the pump beamlet 274 is detected by a detector 294. The reflections of the probe beamlets 276, 278, 280 are detected by appropriately positioned detectors 296, 298, 300, respectively. In embodiments where the detectors 296, 298, 300 function as dark-field detectors, they should be photomultiplier tubes. When the detectors 296, 298, 300 detect specular reflections, they may be photomultiplier tubes, but preferably are PIN diodes in order to achieve a high dynamic range, due to the relatively large signal from the reflected beamlets.

In the above disclosure the collecting optics 288, 290 292 are positioned within the specular angular range of their respective probe beamlets 276, 278, 280 in order to evaluate reflected light. Alternatively, the collecting optics 288, 290, 292 can be positioned outside the specular angular range of all the probe beamlets 276, 278, 280, in which case the detectors 296, 298, 300 function as dark-field detectors. In such embodiments, separate collection optics (not shown) may be provided for the detector 294, or the detector 294 may even be omitted.

In some embodiments the probe beamlets 276, 278, 280 may be temporally distributed, as disclosed in various embodiments herein, for example the system 170 (FIG. 8).

In other embodiments of the subsystem 272, the probe beamlets 276, 278, 280 may simultaneously arrive at the substrate 60 at the same or different spots, which simplifies the beam processing optics.

Operation.

Figure 16:
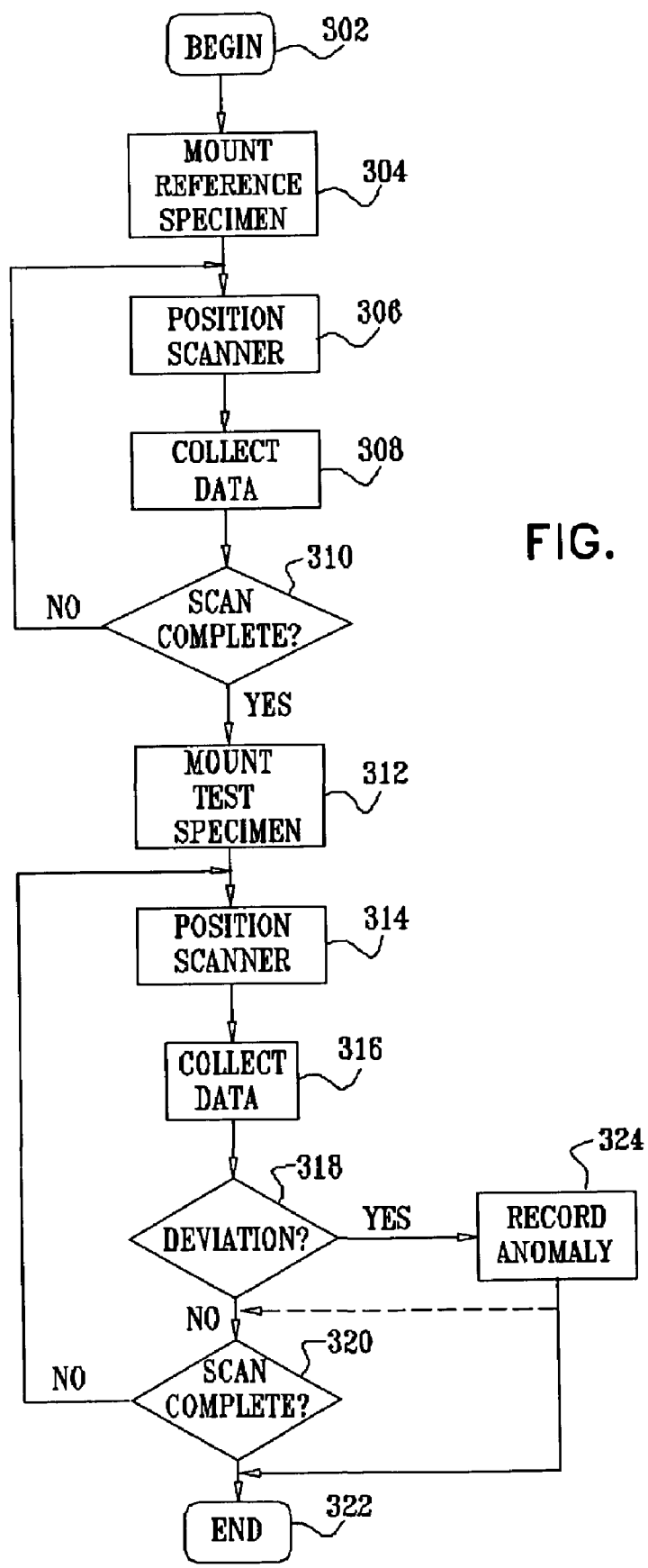
FIG. 16 is a flow chart illustrating a method of detecting buried defects in opaque films in accordance with a disclosed embodiment of the invention.

Reference is now made to FIG. 16, which is a flow chart illustrating a method of detecting buried defects in opaque films in accordance with a disclosed embodiment of the invention. The process begins at initial step 302, in which an apparatus constructed according one of the embodiments described above is configured.

Next, at step 304, a reference specimen is mounted on the apparatus.

Next, at step 306, the specimen is scanned to a point of interest. In some applications all points of the specimen may be scanned at a predetermined resolution, while in other applications, only selected points of interest are evaluated.

Next, at step 308, data is collected from the point at which the scanner was positioned at step 306. The specimen is irradiated by a pump beamlet as described herein, and then by a succession of probe beamlets, according to any of the embodiments disclosed hereinabove. In some applications only one probe beamlet suffices. No more than three probe beamlets are necessary in any case, according to the invention. The raw data taken from the photodetectors may be stored. Alternatively, the raw data may be normalized and stored for ease of comparison with test specimens. Alternatively, a decay constant may be computed in accordance with Equation (1) or Equation (2) and stored. Whichever approach is selected, data from test specimens is treated identically, as explained hereinbelow.

Control now proceeds to decision step 310, where a determination is made whether more points of the reference specimen remain to be evaluated. If the determination at decision step 310 is affirmative, then control returns to step 306.

If the determination at decision step 310 is negative, then control proceeds to step 312, where a test specimen is mounted on the apparatus in the same manner as the reference specimen in step 304.

Next, at step 314, the scanner is positioned. The same scanning operations are executed in step 314 as were performed in step 306, so as to evaluate corresponding points of the test and reference specimens.

Next, at step 316, data is collected from the current point of the test specimen in the same manner as was done in step 308, the details of which are not repeated.

Control now proceeds to decision step 318, where a comparison of the data obtained in step 316 is made with data from the corresponding point of the reference specimen. The statistical methods taught in the above noted application Ser. No. 10/097,442 may be used for the comparison. Alternatively data reduction methods employing Equation (2) may be used. In any case, the result is compared with a predetermined tolerance or standard, which is application specific, and it is determined if the measurement at the current point exceeds the predetermined tolerance.

If the determination at decision step 318 is affirmative, then control proceeds to step 324, which is disclosed hereinbelow.

If the determination at decision step 318 is negative, then control proceeds to decision step 320, where a determination is made whether more points of the test specimen remain to be evaluated.

If the determination at decision step 320 is affirmative, then control returns to step 314.

If the determination at decision step 320 is negative, then control proceeds to final step 322, and the procedure terminates. Subsequent test specimens may be evaluated by entering the flow chart at step 312, as the reference data need not be generally recollected, provided that manufacturing conditions are unchanged.

Step 324 is performed if the determination at decision step 318 is affirmative. It is concluded that an anomaly is present. No further steps need be taken to characterize the anomaly. In a production line environment, it may be required to immediately reject the test specimen as being of substandard quality. Accordingly, control proceeds to final step 322, as there is no need to delay production by continuing the scan. Alternatively, it may be desirable to identify all anomalies of the test specimen in order to adjust the manufacturing process more efficiently, or for other purposes of evaluation. In such applications control proceeds to decision step 320, as indicated by a dotted line in the flow chart of FIG. 16.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An optical apparatus for evaluating a sample, comprising:
    beam processing optics for dividing a beam of pulsed light into a pump beamlet and a plurality of temporally dispersed probe beamlets, said pump beamlet impinging on said sample for transient excitation thereof, said probe beamlets each impinging on said sample subsequent to impingement thereon by said pump beamlet;
    a light detector disposed in a return path of at least one of said probe beamlets; and
    an analyzer, receiving a signal from said detector that is responsive to light detected therein for comparing said signal with a corresponding signal obtained from a reference sample, wherein a presence of an anomaly in said sample is indicated by a deviation of said signal from said corresponding signal.

2. The optical apparatus according to claim 1, wherein said plurality of temporally dispersed probe beamlets is exactly three probe beamlets that impinge on said sample at different times.

3. The optical apparatus according to claim 1, wherein said plurality of temporally dispersed probe beamlets is exactly two probe beamlets that impinge on said sample at different times.

4. The optical apparatus according to claim 1, wherein said analyzer is adapted to compare a first degree exponential decay of said signal with a first degree exponential decay of said corresponding signal.

5. The optical apparatus according to claim 1, further comprising a scanning mechanism, for scanning said pump beamlet and at least one of said plurality of temporally dispersed probe beamlets over said sample.

6. The optical apparatus according to claim 1, wherein said light detector is disposed in a return path of said pump beamlet.

7. The optical apparatus according to claim 1, wherein pulses of said light have a duration between about 100 fsec and 3 psec.

8. The optical apparatus according to claim 1, wherein pulses of said light have a duration between about 100 fsec and 1 nsec.

9. The optical apparatus according to claim 1, wherein said pump beamlet is incident normal to a surface of said sample.

10. The optical apparatus according to claim 1, wherein said pump beamlet is incident oblique to a surface of said sample.

11. The optical apparatus according to claim 1, wherein said beam processing optics process said pump beamlet and said plurality of temporally dispersed probe beamlets by wavelength.

12. The optical apparatus according to claim 1, wherein said beam processing optics include a second harmonic generator crystal disposed in an optical path of said beam.

13. The optical apparatus according to claim 1, wherein said beam processing optics comprises:
a plurality of reflective edge filters disposed in a path of said beam;
a plurality of retroreflectors, each of said retroreflectors reflecting one of said probe beamlets; and
a dichroic mirror, receiving said pump beamlet and receiving said probe beamlets via said retroreflectors, for combining said probe beamlets with said pump beamlet.

14. The optical apparatus according to claim 1, wherein said beam processing optics comprises:
a plurality of reflective edge filters disposed in a path of said beam; a plurality of retroreflectors, each of said retroreflectors reflecting one of said temporally dispersed beamlets; and
focusing optics disposed in paths of said temporally dispersed beamlets, wherein said temporally dispersed beamlets impinge on said sample at different angles of incidence.

15. The optical apparatus according to claim 1, wherein said detector comprises a first detector disposed within a specular angular range of at least one of said plurality of temporally dispersed probe beamlets and a second detector disposed outside said specular angular range thereof.

16. The optical apparatus according to claim 1, wherein said plurality of temporally dispersed probe beamlets comprises a first probe beamlet and a second probe beamlet, a wavelength of said first probe beamlet differing from a wavelength of said second probe beamlet, further comprising wavelength-responsive collection optics for said first probe beamlet and said second probe beamlet, said collection optics projecting said first probe beamlet in a first return path from said sample and projecting said second probe beamlet in a second return path from said sample; and
wherein said detector comprises a first detector disposed in said first return path and a second detector disposed in said second return path.

17. The optical apparatus according to claim 16, wherein a collection lens of said collection optics is disposed within a specular angular range of said first probe beamlet and within a specular angular range of said second probe beamlet.

18. The optical apparatus according to claim 16, wherein a collection lens of said collection optics is disposed without a specular angular range of said first probe beamlet and without a specular angular range of said second probe beamlet.

19. The optical apparatus according to claim 16, wherein said collection optics are disposed within a third return path from said sample of said pump beamlet, and further comprising a third detector disposed in said third return path.

20. The optical apparatus according to claim 16, wherein said collection optics comprises a plurality of reflective edge filters.

21. The optical apparatus according to claim 16, wherein said collection optics comprises a prism.

22. The optical apparatus according to claim 16, wherein said collection optics comprises a diffractive grating.

23. The optical apparatus according to claim 1, wherein said plurality of temporally dispersed probe beamlets comprises a first probe beamlet and a second probe beamlet, an angle of incidence with said sample of said first probe beamlet differing from an angle of incidence with said sample of said second probe beamlet, further comprising first collection optics and second collection optics that respectively project said first probe beamlet in a first return path from said sample and said second probe beamlet in a second return path from said sample; and
wherein said detector comprises a first detector disposed in said first return path and a second detector disposed in said second return path.

24. The optical apparatus according to claim 23, wherein a collection lens of said first collection optics is disposed within a specular angular range of said first probe beamlet and a collection lens of said second collection optics is within a specular angular range of said second probe beamlet.

25. The optical apparatus according to claim 23, wherein a collection lens of said first collection optics is disposed without a specular angular range of said first probe beamlet and a collection lens of said second collection optics is disposed without a specular angular range of said second probe beamlet.

26. The optical apparatus according to claim 23, wherein said detector further comprises third collection optics that project said pump beamlet in a third return path from said sample, and further comprising a third detector disposed in said third return path.

27. A method for evaluating a sample, comprising the steps of:
impinging a pump beamlet of pulsed light on an area of said sample for transient excitation thereof;
thereafter impinging a plurality of temporally dispersed probe beamlets on an excited area of said sample;
detecting returning light of said plurality of temporally dispersed probe beamlets from said sample;
comparing said returning light of instances of said plurality of temporally dispersed probe beamlets with one another; and
responsively to said step of comparing reporting an anomaly of said sample upon detection of a difference between said returning light of said instances of said plurality of temporally dispersed probe beamlets.

28. The method according to claim 27, wherein said plurality of temporally dispersed probe beamlets is exactly two probe beamlets.

29. The method according to claim 27, wherein said plurality of temporally dispersed probe beamlets is exactly three probe beamlets.

30. The method according to claim 27, wherein said step of comparing comprises computing a time related function of said returning light of said instances of said plurality of temporally dispersed probe beamlets.

31. The method according to claim 30, wherein said time related function is a first degree exponential decay curve.

32. The method according to claim 31, further comprising the step of determining a decay constant of said curve.

33. The method according to claim 27, wherein pulses of said light have a duration between about 100 fsec and 3 psec.

34. The method according to claim 27, wherein pulses of said light have a duration between about 100 fsec and 1 nsec.

35. The method according to claim 27, wherein said pump beamlet is incident normal to a surface of said sample.

36. The method according to claim 27, wherein said pump beamlet is incident oblique to a surface of said sample.

37. The method according to claim 27, further comprising the step of processing said pump beamlet and said plurality of temporally dispersed probe beamlets by wavelength.

38. The method according to claim 27, wherein said step of impinging a plurality of temporally dispersed probe beamlets is performed by:
projecting said temporally dispersed probe beamlets along optical paths, each of said paths extending to said sample, and each of said paths having a different length, wherein said temporally dispersed probe beamlets impinge on said sample at different angles of incidence.

39. The method according to claim 38, wherein said step of detecting returning light further comprises detecting a first light of a first one of said temporally dispersed probe beamlets in a first return path from said sample and detecting a second light of a second one of said temporally dispersed probe beamlets in a second return path from said sample.

40. The method according to claim 39, wherein at least a portion of said first return path lies within a specular angular range of said first one of said temporally dispersed probe beamlets and at least a portion of said second return path lies within a specular angular range of said second one of said temporally dispersed probe beamlets.

41. The method according to claim 39, wherein at least a portion of said first return path lies without a specular angular range of said first one of said temporally dispersed probe beamlets and at least a portion of said second return path lies without a specular angular range of said second one of said temporally dispersed probe beamlets.

42. The method according to claim 38, wherein said step of detecting returning light further comprises detecting a third light of said pump beamlet in a third return path from said sample.

43. The method according to claim 27, wherein a wavelength of said pump beamlet differs from a wavelength of said plurality of temporally dispersed probe beamlets, and said step of detecting returning light is performed by:
detecting a first light in a first return path of said pump beamlet from said sample; and
detecting a second light in a second return path of at least one of said plurality of temporally dispersed probe beamlets from said sample, wherein a portion of said first return path avoids said second return path.

44. The method according to claim 43, wherein said first return path and said second return path share a common segment, and said step of detecting returning light further comprises processing said at least one of said plurality of temporally dispersed probe beamlets and said pump beamlet in said common segment according to wavelength.

45. The method according to claim 44, wherein said common segment is disposed within a specular angular range of said pump beamlet and within a specular angular range of said at least one of said plurality of temporally dispersed probe beamlets.

46. The method according to claim 44, wherein said common segment is disposed without a specular angular range of said pump beamlet and without a specular angular range of said at least one of said plurality of temporally dispersed probe beamlets.

* * * * *